(12) United States Patent
Reinhardt et al.

(10) Patent No.: US 9,173,816 B2
(45) Date of Patent: Nov. 3, 2015

(54) CLOSED SYSTEM TRANSFER DEVICE AND AUTOMATION SYSTEM

(71) Applicant: Intelligent Hospital Systems, Inc., Winnipeg (CA)

(72) Inventors: Alex H. Reinhardt, St. Andrews (CA); Ronald H. Rob, Dugald (CA)

(73) Assignee: Intelligent Hospital Systems, Inc., Winnipeg, Manitoba ( * ) Notice: Subject to any disclaimer, the term of this patent is extended or adjusted under 35 U.S.C. 154(b) by 0 days.

(21) Appl. No.: 13/950,061

(22) Filed: Jul. 24, 2013

(65) Prior Publication Data

US 2014/0031976 A1    Jan. 30, 2014

Related U.S. Application Data

(60) Provisional application No. 61/675,026, filed on Jul. 24, 2012.

(51) Int. Cl.
*A61J 1/20* (2006.01)
*A61J 1/00* (2006.01)
*A61J 3/00* (2006.01)

(52) U.S. Cl.
CPC .... *A61J 1/20* (2013.01); *A61J 1/00* (2013.01); *A61J 3/002* (2013.01)

(58) Field of Classification Search
CPC ............ A61J 1/00; A61J 1/05; A61J 1/10; A61J 1/20; A61J 3/002; A61M 37/00; G06F 19/34; G06F 19/3456; G06F 19/3468
USPC .......................................... 141/329; 700/239
See application file for complete search history.

(56) References Cited

U.S. PATENT DOCUMENTS

| | | | |
|---|---|---|---|
| 4,842,028 A | 6/1989 | Kaufman et al. | |
| 7,117,902 B2* | 10/2006 | Osborne | 141/27 |
| 7,610,115 B2 | 10/2009 | Rob et al. | |
| 7,717,897 B2* | 5/2010 | Burg et al. | 604/408 |
| 7,783,383 B2 | 8/2010 | Eliuk et al. | |
| 7,930,066 B2 | 4/2011 | Eliuk et al. | |
| 7,931,859 B2 | 4/2011 | Mlodzinski et al. | |
| 8,151,835 B2 | 4/2012 | Khan et al. | |
| 8,182,744 B2 | 5/2012 | Mlodzinski et al. | |
| 8,225,824 B2 | 7/2012 | Eliuk et al. | |
| 8,267,129 B2 | 9/2012 | Doherty et al. | |
| 8,271,138 B2 | 9/2012 | Eliuk et al. | |
| 2003/0236501 A1* | 12/2003 | Donnan et al. | 604/192 |
| 2006/0136095 A1 | 6/2006 | Rob et al. | |
| 2006/0259195 A1 | 11/2006 | Eliuk et al. | |

(Continued)

OTHER PUBLICATIONS

International Search Report and Written Opinion issued Oct. 8, 2013 in PCT/CA2013/000666.

*Primary Examiner* — Jerrah Edwards
*Assistant Examiner* — Tamara Weber
(74) *Attorney, Agent, or Firm* — Reinhart Boerner Van Deuren s.c.

(57) ABSTRACT

A robotic intravenous automation system, including a robotically controlled holder configured to manipulate an intravenous (IV) bag and a closed system transfer device (CSTD). The controller includes a processor configured to control the holder. The IV bag includes a first fluid port and a second fluid port, and the CSTD includes a CSTD port, a spike adapter that is fluidically separated from the CSTD port, and a flexible member connecting the CSTD port to the spike adapter.

24 Claims, 16 Drawing Sheets

(56) References Cited

U.S. PATENT DOCUMENTS

| | | |
|---|---|---|
| 2008/0051937 A1 | 2/2008 | Khan et al. |
| 2008/0114328 A1 | 5/2008 | Doherty et al. |
| 2008/0199353 A1 | 8/2008 | Mlodzinski et al. |
| 2009/0067973 A1 | 3/2009 | Eliuk et al. |
| 2009/0126825 A1 | 5/2009 | Eliuk et al. |
| 2010/0017031 A1 | 1/2010 | Rob et al. |
| 2010/0198392 A1 | 8/2010 | Eliuk et al. |
| 2011/0098669 A1* | 4/2011 | Boyes ............ 604/411 |
| 2011/0172810 A1 | 7/2011 | Mlodzinski et al. |
| 2011/0208350 A1 | 8/2011 | Eliuk et al. |
| 2012/0046636 A1* | 2/2012 | Kriheli ............ 604/414 |

* cited by examiner

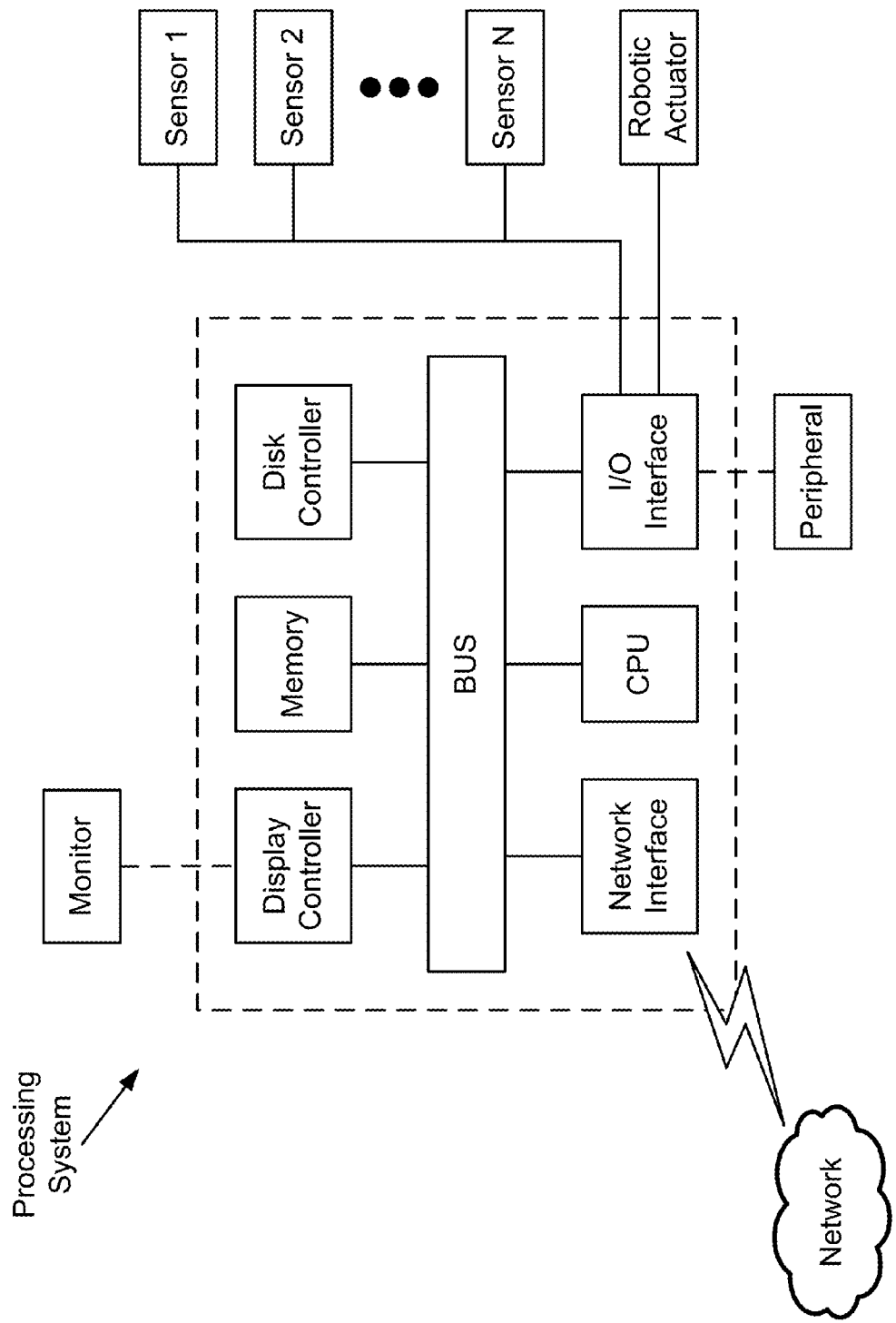

CLOSED SYSTEM TRANSFER DEVICE AND AUTOMATION SYSTEM

CROSS-REFERENCE TO RELATED APPLICATIONS

This application relates to and incorporates by reference the disclosures of U.S. 61/675,026, filed Jul. 24, 2012, U.S. Pat. No. 7,610,115 B2, filed Dec. 22, 2005, U.S. Pat. No. 7,783,383 B2, filed Mar. 27, 2006, US 2008/0114328 A1, filed Nov. 9, 2007, and US 2009/0067973 A1, filed Sep. 11, 2008.

BACKGROUND

Closed system transfer devices (CSTDs) are devices that are used with transferring usually hazardous pharmaceutical agents that can result in contamination. CSTDs allow for a transfer of the pharmaceutical agents, such as a fluid containing hazardous medicine, between medical containers under a closed condition.

SUMMARY OF ILLUSTRATIVE EMBODIMENTS

A robotic intravenous automation (RIVA) system, can include a robotically controlled holder configured to manipulate an intravenous (IV) bag and a closed system transfer device (CSTD), and can further include a controller including a processor configured to control the holder. The holder can be a robotic arm.

The IV bag can include a first fluid port and a second fluid port. The CSTD can include a CSTD port, a spike adapter that is fluidically separated from the CSTD port, and a flexible member connecting the CSTD port to the spike adapter. The first and second fluid ports can be joined together to the spike adapter and the CSTD port to form a CSTD assembly.

The controller can be configured to control the holder to perform a process of attaching the spike adapter to the first fluid port of the IV bag, grasping the CSTD port based on a predefined dimensional characteristic of the CSTD stored in the controller, manipulating the CSTD port, flexing the flexible member; and attaching the CSTD port to the second fluid port of the IV bag.

The controller can be configured to control the holder to perform a process of accepting a user command to prepare an IV bag with a particular drug, determining whether the particular drug requires a CSTD, and selecting, by the holder, the CSTD IV bag assembly based on the determining. The process can further include attaching a CSTD syringe containing the particular drug to the CSTD port, and performing a fluid transfer of the particular drug between the CSTD syringe and the IV bag via the CSTD port. The process can further include outputting an indication to place the CSTD IV bag assembly into an inventory rack of the system, and verifying the CSTD IV bag assembly has been placed into the inventory rack of the system. The verifying can include a visual-based verification by image analysis, or an RFID-based verification.

The controller can be configured to control the holder to perform a process of testing an attachment of the CSTD port to the second fluid port of the IV bag by pulling the CSTD port away from the second fluid port of the IV bag and measuring a amount of force applied in the pulling, and stopping the testing when the amount of force reaches a predefined amount. The predefined amount can be 5, 10, 20, or 40 lbs. The process can further include attaching a CSTD syringe to the CSTD port, and performing a fluid transfer between the CSTD syringe and the IV bag via the CSTD port and the second fluid port of the IV bag.

The first fluid port of IV bag can have a different shape than the second fluid port of the IV bag, and the controller can be configured to distinguish between the first and second fluid ports by a sensor. The second fluid port of the IV bag can be a needle port, whereas the first fluid port of the IV bag may not be a needle port.

The CSTD port can include an alignment structure that coincides with a particular alignment between the CSTD port and the spike adapter, in which the holder and controller can distinguish the particular alignment by holding the CSTD by the alignment structure. The alignment structure can serve as a grasping point for manipulating a CSTD IV bag assembly by the holder.

The CSTD port can include a cannula, and the CSTD port can include reverse facing barbs on an interior portion thereof that contacts an exterior of the first or second fluid port of the IV bag that can positively lock the CSTD port to the first or second fluid port of the IV bag. The spike adapter can include two membranes.

The flexible member can have a relatively long, thin and wide cross section that can inhibit selected movement between the CSTD port and the spike adapter. The flexible member can resist a relative twisting motion between the CSTD port and the spike adapter, so that the CSTD port and the spike adapter can have a natural un-stressed position of having parallel axes, with respect to a long axis of each of the CSTD port and the spike adapter.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 9 schematically illustrates a processing system for a controller and/or a computer system;

DETAILED DESCRIPTION

Figure 1:
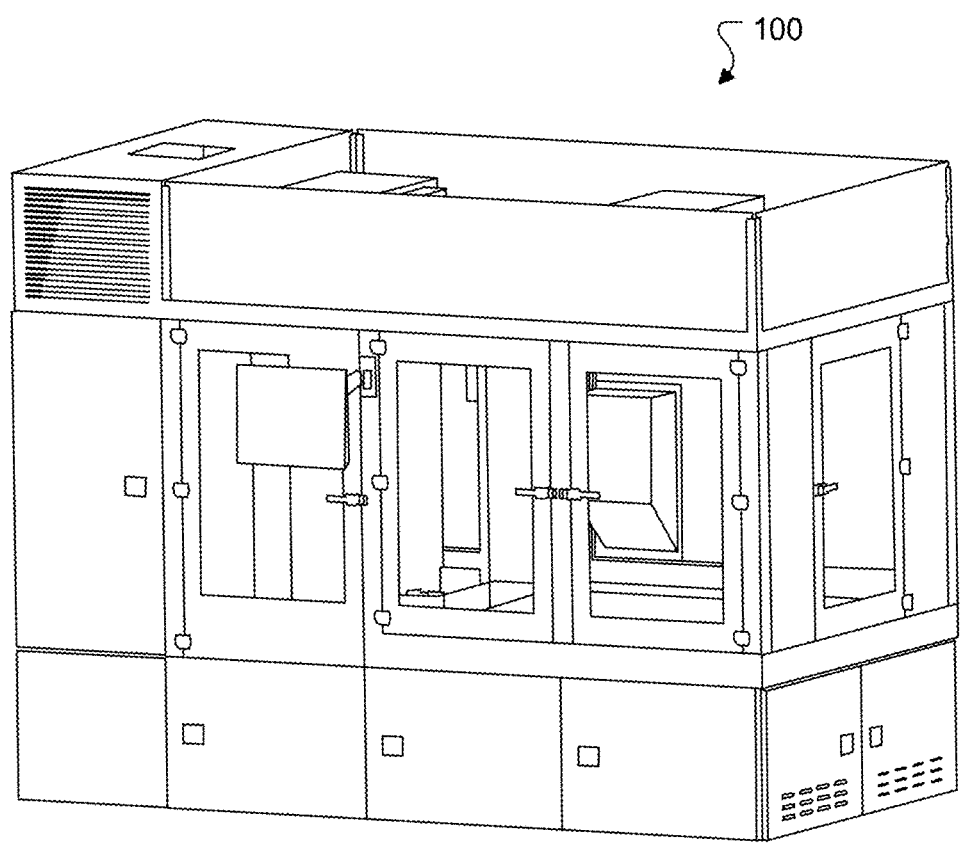
FIG. 1 shows an illustrative system.

In the drawings, like reference numerals designate identical or corresponding parts throughout the several views.

Various illustrative embodiments relate to processing medical items contained in medical containers, such as bags, vials, and syringes. Some embodiments involve automation of processes to transfer fluids, compound pharmaceuticals and/or package and prepare medical items into medical containers. An Automated Pharmacy Admixture System (APAS), sometimes referred to herein as a Robotic IV Automation system (RIVA), may include a manipulator that transports medical containers such as bags, vials, or syringes about a substantially aseptic admixing chamber. A RIVA automates the preparation of IV (intravenous) admixtures in medical containers.

This disclosure describes systems and techniques for controlling fluid transfer operations among medicinal containers such as syringes, vials, and IV bags. The systems and techniques may be used during admixture or compounding and dispensing of drug doses, such as in an APAS or a RIVA. An example thereof is described with reference to FIGS. 1-5 in U.S. Pat. No. 7,610,115 B2, filed Dec. 22, 2005, and with reference to FIGS. 1-5 in U.S. Pat. No. 7,783,383 B2, filed Mar. 27, 2006, the entire contents of each of which are herein incorporated by reference. An example of an apparatus for controlling fluid transfer between a fluid transfer device and a container or conduit is described with reference to FIGS. 1-7 in US 2008/0114328 A1, filed Nov. 9, 2007, the entire contents of which are herein incorporated by reference.

FIG. 1 shows an illustrative APAS or RIVA 100 for use within a hospital pharmacy environment, which may autonomously admix contents of syringes and IV bags using automation technologies. For example, embodiments of the RIVA 100 may perform one or more operations that might otherwise be performed by pharmacy staff within a laminar airflow hood. The RIVA 100 includes a robotic cell that automates the compounding and dispensing of drug doses into IV bags and/or syringes, such as those that may be prepared in hospital pharmacies. The robotic cell may use a syringe-based fluid transfer process, and may employ a robotic manipulator (e.g., a multiple degree of freedom arm) for moving drug vials, syringes, and IV bags through the cell as the medications are processed.

Figure 2:
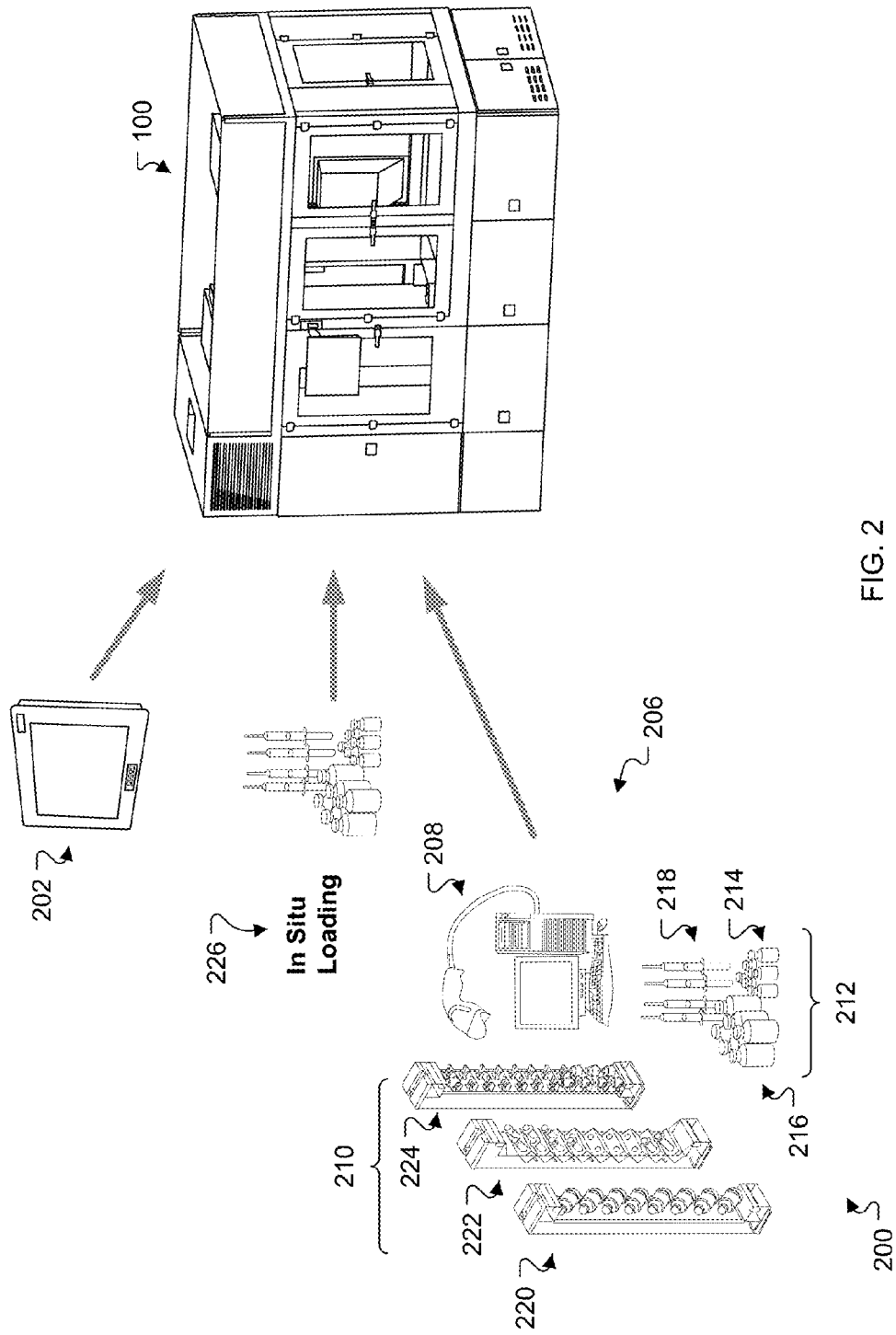
FIG. 2 shows an illustrative inventory system for the system of FIG. 1.

FIG. 2 shows illustrative equipment 200 that allows an operator to load inventory, input control information, and/or retrieve syringes and/or IV bags from the RIVA 100 of FIG. 1. The RIVA 100 includes a flat panel monitor 202 which may be used by an operator, for example a pharmacy technician, as a user interface to the RIVA 100. The RIVA 100 may include one or more flat panel monitors 202, which may be used to input control information and/or output status information, for example. In this example, the flat panel monitor 202 may also act as a control device to allow the operator, for example by touching the indicators on a touch screen, to start, stop, and pause the RIVA 100. As an output device, the flat panel monitor 202 can be used in the monitoring of the status and alarm conditions of the RIVA 100 by displaying, for example, a message to the operator when a predetermined condition has occurred. As another example, an operator may use the flat panel monitor 202 to control the process of loading the RIVA 100 with the drugs needed to perform its compounding process. The operator may use the flat panel monitor 202 as an input device, for example, to control the cleaning of the RIVA 100 in a step-by-step manner. The flat panel monitor 202 may be used as an input and output device, for example, by a pharmacy technician while training the system for new drugs that are to be prepared in the RIVA 100.

In conjunction with the RIVA 100, a remote user station (RUS) 206 may provide inventory control, planning, and/or management and management functions. The RUS 206 may include a workstation 208, inventory racks 210, and inventory (e.g., drug containers) 212. The workstation 208 may be interfaced to the RIVA 100, either directly or through a computer network (e.g., LAN, WAN, MAN, wLAN), which may be part of a hospital interface network in some implementations. The operator, for example, may use the workstation 208 to review, add to, prioritize, or amend drug orders and planned production for the RIVA 100. The operator may also use the workstation 208 to plan and manage the compounding and/or dispensing of drug dosages by the RIVA 100, and/or to report operations with regard to such processes. In another example, the workstation 208 may be used in RIVA management to control the release of drug order queues to cells for the compounding process, or to monitor the RIVA 100 status during the compounding process.

The workstation 208, and/or the RIVA 100, may include hardware and/or software executed by a computer processor for scanning identifying indicia, such a bar code, RFID tag, etc., to facilitate the identification of inventory, and/or the placement of the inventory on a rack.

In this example, an operator may use the RUS 206 to coordinate the loading of inventory racks 210. The inventory racks 210 may be loaded with inventory 212, which may include vials of various sizes 214, 216, syringes 218 and/or IV bags (not shown). In this embodiment, each of the racks 210 may store only one type or size of inventory items; however, different racks may be arranged to hold inventory items of various sizes. In some embodiments, one or more of the racks 210 may be configured to store multiple sizes and/or types of inventory items. In this embodiment, the racks 210 are arranged to store large vials 220, syringes 222, or small vials 224. Further embodiments of racks 210 for storing inventory may include racks for IV bags, and examples of such racks are described with reference to U.S. Pat. No. 7,783,383 B2 at FIGS. 5 and 14, for example. Each inventory item may be manually placed within an appropriate support, which may include, for example, a retention clip, hook, shelf, bin, slot, or pocket on the rack 210.

The inventory 212 may be used as inputs to the RIVA 100, supplying it with vials, syringes, and/or IV bags that may contain drugs and/or diluents needed by the system for the compounding process. The RIVA 100 may output syringes and/or IV bags that have been prepared for use, for example, in dispensing drug doses to patients in a hospital, health care facility, clinic, or for distribution on an outpatient basis (e.g., in-home nurse visits).

In some implementations, the inventory racks 210 may be pre-loaded (e.g., off-line in advance) with the inventory 212 needed for input to the RIVA 100. For example, pre-loaded racks of commonly used inputs (e.g., saline IV bags) may be prepared to satisfy anticipated, expected, or planned compounding production orders. Preloading may occur, for example, in an off-site warehouse where the racks, drug inventory, and container inventory may be stored. Some or all operations relating to the remote workstation may be performed in work areas that have a controlled environment, which may be a substantially aseptic environment. The computer device 208 may communicate with the RIVA 100, and each may be programmed to process and/or exchange information about historical, current, and anticipated inventory, supply schedules, and demand information. The information may be used to prioritize, schedule, and order inventory to respond to and satisfy production input requirements for one or more RIVA 100 systems, for example. In some cases, the RIVA 100 may coordinate with a hospital inventory control system to place orders automatically, for example, to maintain a minimum level of inventory of certain inputs or outputs of the RIVA 100 based on historical and expected demand information.

In some examples, the RIVA 100 may be operated in a batch mode to produce some number of substantially similar outputs, such as cefazolin at a particular dose and in a particular type of syringe. In other examples, the RIVA 100 may be operated to be loaded with inventory in situ 226. In situ loading may occur at substantially any time to produce a typically limited number of outputs, which may include a single dose, for example. In situ loading may involve, for example, loading inventory onto a rack in the RIVA 100 without interrupting an on-going compounding process, or when the RIVA 100 is in an idle mode.

Some embodiments may include two independently operable carousels. In one mode of operation, one of the carousels can be operating to deliver inventory to the processing chamber while the other carousel is being unloaded or loaded. In a further embodiment, the RIVA 100 may include three or more inventory delivery systems, which may perform the same functions as the carousels, examples of which are described elsewhere herein. In such embodiments, one or more of the carousels may be operated to deliver inventory while one or more other carousels are being serviced or loaded/unloaded with inventory.

For example, a pharmacy technician may use in situ loading of the RIVA 100 in response to a written or electronically received order from a physician for a medication that is needed quickly (which may be referred to as a stat order or an on-demand order). The RIVA 100 may notify the technician what inputs need to be loaded to fulfill the order. Knowing the items needed for the stat order, the technician may load any inventory (e.g., drug vial, syringe, and/or IV bag) to perform the compounding and/or dispensing process in the appropriate rack(s) 210 and places the rack(s) 210 onto a carousel (not shown here) in the RIVA 100. In another embodiment, the technician may load the inventory into unused locations in one or more racks that are already on a carousel in the RIVA 100. The technician may input order information or instructions to configure the RIVA 100 to prepare to fulfill the stat order.

In some examples, the RIVA 100 may have stored in a memory or a database a recipe for compounding. In such cases, the operator may identify the recipe to be recalled from memory. In other examples, a pharmacy technician or operator may teach the RIVA 100 how to process the inventory using a software-driven user interface, for example. The RIVA 100 may learn new recipes through a training mode, which may involve the user entering command information via a graphical user interface being displayed on the monitor 202. The operator may, for example, indicate locations of inventory items on a graphical map of the inventory system.

In some embodiments, storage racks may be scanned with a scanner (e.g., bar-code, RFID, etc.) when re-stocking inventory. Reports that may be printed by the RIVA or by printers associated with networked computers (e.g., hospital pharmacy data input terminals) may include bar-coded information that can be cross-referenced when, for example, distributing drugs (e.g., to patients, hospital carts, etc.). Data stored in a memory accessible by a computer system may include data associated with medical items, authorized system users and associated access rights, storage areas, and restock information. Authorized user information may be associated with user identification information, such as biometric data, passwords, challenge-response authentication, as well as other mechanisms known to those of ordinary skill in the art. In some implementations, at least in some modes, access to the storage chamber requires an authorized user to enable access to the doors, which may be unlocked in response to an authorized request for access.

Stored data may also include machine readable indicia (e.g., 1 or 2 dimensional bar codes, RFID tag codes, etc.), text which may be read using OCR (optical character recognition), and/or voice recognition information. Stored data about medical items may be include brand name and/or generic name information. Medical containers, including IV bags, vials, and/or syringes, may be labeled with such data in connection with restocking inventory in a storage carousel or storage rack, for example, or in connection with an output of a medical item individually or as a kit.

Figure 3:
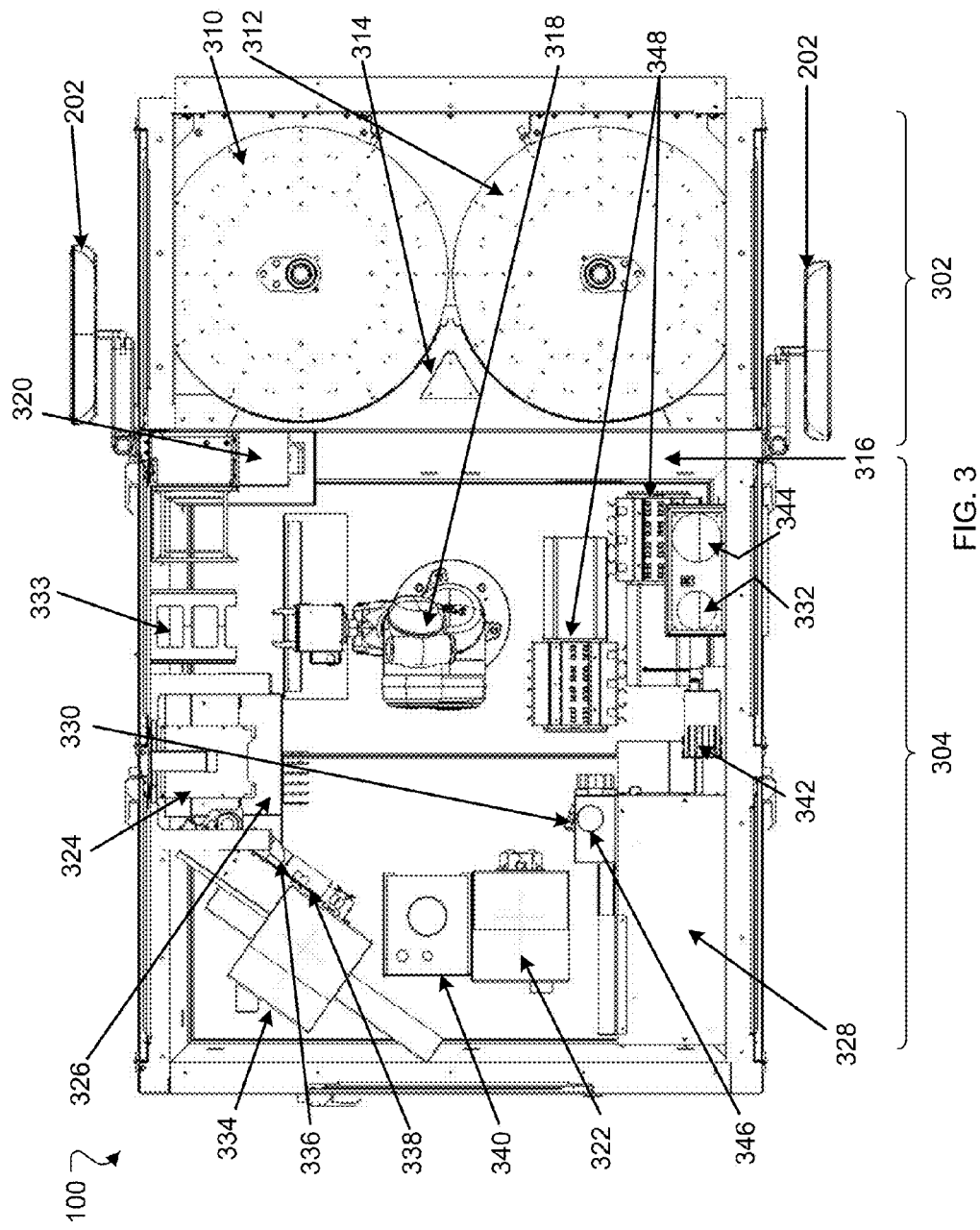
FIG. 3 shows a top cut-away view of the system of FIG. 1.

FIG. 3 shows an illustrative top cut-away view of the RIVA 100 of FIG. 1. The RIVA 100 includes two chambers. An inventory chamber 302 is used as an inventory loading area, which can be accessed by an operator to load the RIVA 100 through a loading door (not shown). A processing chamber 304 includes the compounding area in which the admixture and/or compounding processes may occur. In some embodiments, the processing chamber 304 provides a substantially aseptic environment, which may be an ISO Class 5 environment that complies with clean room standards. Mounted on the exterior of the RIVA 100 are two of the monitors 202, which may serve as input/output devices as described with reference to FIG. 2.

The inventory chamber 302 includes two inventory rack carousels 310 and 312 and a temporary inventory rack 314. The temporary inventory rack 314 may be used to locate in-process drug vials that contain enough material to provide multiple doses. Each inventory rack carousel 310 may support multiple inventory racks 210. In some applications, an operator may remove one or more racks from the carousels 310, 312 and replace them with racks loaded with inventory. The racks may be loaded onto the carousels 310, 312 according to a load map, which may be generated by the operator for submission to the RIVA 100, or generated by the RIVA 100 and communicated to the operator. The chambers 302, 304 are separated by a dividing wall 316, an example of which is described with reference to FIG. 4.

The processing chamber 304 includes a multiple degree of freedom robotic arm 318, and the robotic arm 318 further includes a gripper that can be used, for example, to pick items from a pocket on a rack or to grasp items within the RIVA 100 for manipulation. An illustrative gripper is described in further detail in U.S. Pat. No. 7,783,383 B2 with reference to FIGS. 9-11. The robotic arm 318 may respond to command signals from a controller (described later) to pick up, manipulate, or reposition inventory items within the processing chamber 304, and in or around the carousels 310, 312. The robotic arm 318 may manipulate inventory items, for example, by picking a vial, IV bag, or syringe from a rack of the carousels 310, 312 in the inventory chamber 302, and moving the item to a station in the processing chamber 304 for use in compound preparation. In some examples, the robotic arm 318 may manipulate inventory items on the carousels 310, 312 through access port 410 in the dividing wall 316. The dividing wall 316 may be substantially sealed so that a substantially aseptic environment may be maintained for compounding processes in the processing chamber 304.

According to an illustrative example, an incoming drug order from the RUS 206 involves a batch production order for syringes to be charged with individual doses of a drug that is reconstituted from a drug provided in one or more vials. The operator, for example, may preload the drug into the RIVA 100 during a loading process by loading the carousel 310 with inventory racks of the drug vials, and by interfacing with the RIVA 100 using the input/output device 202 to initiate, monitor, and/or control the loading process. As the RIVA 100 is processing a previous order, the operator may load the carousel 312 with inventory racks of syringes, drug vials, and IV bags for the next batch production order while the RIVA 100 is operating the carousel 310. Once the loading process is complete, the operator may submit the batch production process, which may begin immediately, or after other processing is completed.

To execute the batch production, in this example, the robotic arm 318 may pick a syringe from a pocket in a rack in carousel 310. The syringe in the carousel may have a needle and a needle cap. The needle cap is removed for processing in the RIVA 100. The robotic arm 318 may convey the syringe to a decapper/deneedler station 320 where the needle cap is removed from the syringe/needle assembly to expose the needle. The robotic arm 318 may transfer the syringe to a needle-up syringe manipulator 322 where a dose of the drug is drawn from a vial, which was previously placed there by the robotic arm 318 after one or more verification operations (e.g. weighing, bar code scanning, and/or machine vision recognition techniques). The robotic arm 318 moves the syringe to the decapper/deneedler station 320 where the needle is removed from the syringe and disposed of into a sharps container (not shown here). The robotic arm 318 then moves the syringe to a syringe capper station 324, where the needleless syringe is capped. The robotic arm 318 moves the syringe to a scale station 326 where the syringe is weighed to confirm the predetermined dose programmed into the RIVA 100. The robotic arm 318 then moves the syringe to a printer and labeling station 328 to receive a computer readable identification (ID) label that is printed and applied to the syringe.

This label may have a bar code or other computer readable code printed on it which may contain, for example, patient information, the name of the drug in the syringe, the amount of the dose, as well as date and/or lot code information for the inputs. The robotic arm 318 then moves the syringe to an output scanner station 330 where the information on the ID label is read by the scanner to verify that the label is readable. The RIVA 100 may report back to the RUS 206 using the hospital interface network, for use in operations planning. The syringe is then taken by the robotic arm 318 and dropped into the syringe discharge chute 332 where it is available to the pharmacy technician, for example, to be placed in inventory within the hospital pharmacy. As the process continues, there may be times during the drug order process where the robotic arm 318 removes an empty vial from the needle up syringe manipulator 322 and places it into a waste chute 333.

In another illustrative example, a syringe may be used for both as an input containing a fluid (e.g., diluent or known drug compound) to be admixed in a compounding process, and as an output containing a prepared dose suitable for delivery to a patient. Such a syringe may be needed to fulfill a special reconstitution order programmed into the RIVA 100 via the input/output capabilities of the monitor 202, for example. In another example, the order may be a stat order, which may be received from a hospital interface. In this example, the operator performs in situ loading 226 by placing the syringes to be used for both reconstitution and dosing in pockets on a rack already located on the carousel 310. The operator enters the reconstitution order into the RIVA 100. The robotic arm 318 picks the selected syringe from a pocket in the rack in the carousel 310 and moves it to the decapper/deneedler station 320, where the needle cap is removed from the syringe/needle combination, thereby exposing the needle. The syringe is then transferred by the robotic arm 318 to a needle down syringe manipulator 334. At the station 334, diluent is drawn into the syringe from a diluent supply IV bag 336 previously placed there by the robotic arm 318. The diluent supply 336 may be contained in an IV bag which is hung on the needle down syringe manipulator 334 by a clip, e.g., consistent with that shown in U.S. Pat. No. 7,783,383 B2 at FIGS. 6-7.

An air extraction process may be performed to prime the IV bag, if needed, the details of which are described in U.S. Pat. No. 7,783,383 B2 with reference to FIGS. 15A-15C. The syringe then punctures the membrane of the diluent port 338 (another example of which is shown in FIG. 7 of U.S. Pat. No. 7,783,383 B2) in a needle down orientation. The syringe is actuated to remove, for example, a predetermined amount of the diluent from the IV bag. The needle down syringe manipulator 334 then moves a reconstitution vial placed there previously by the robotic arm 318, under the syringe. The diluent in the syringe is transferred to the vial for reconstitution with the vial contents. The robotic arm 318 then moves the vial to a mixer for shaking according to a mixing profile. The robotic arm 318 then moves the vial to the needle up syringe manipulator 322 where the appropriate amount of the reconstituted drug is drawn from the vial into an "output" syringe that was previously conveyed there by the robotic arm 318.

In another embodiment, the RIVA 100 may receive a production order to prepare compounds that may involve IV bags as input inventory items or as outputs. In some examples, an IV bag may be selected as a diluent source for reconstitution in a drug order to be output into another medical container. In other examples, the selected IV bag may be used for output after preparation of the drug order is completed. Some IV bags may be placed on the carousel 310, 312 and used as an input that may be at least partially filled with a diluent that may be used to reconstitute drugs. The reconstituted drugs may be output in the form of charged syringes or IV bags. The operator loads racks of syringes and IV bags into the carousel 310 for use in the production order. During the production order, the robotic arm 318 picks an IV bag from a rack on the carousel 310 and moves it to the scale and bag ID station 326. At this station, the IV bag is identified by bar code or pattern matching and its weight is recorded. This may be done, for example, as an error check, and/or to positively identify the type and/or volume of diluent being used for reconstitution. If the IV bag is selected as a diluent source, then the bag may be weighed before use to confirm the presence of the diluent in the IV bag. If the IV bag is selected for output, it may be weighed multiple times, such as before, during, and/or after each fluid transfer step, for example. As a post-transfer verification step, the weight may be re-checked after fluid transfer operations have occurred to determine if the change in weight is within an expected range. Such checks may detect, for example, leaks, spills, overfills, or material input errors. In this example, the robotic arm 318 moves the IV bag to a port cleaner station 340 where a pulsed ultraviolet (UV) light or other sanitizing process may be used to substantially sterilize, disinfect, and/or sanitize at least a portion of the IV bag port. The robotic arm 318 moves the IV bag to the needle up syringe manipulator 322 where a pre-filled syringe has been loaded. As in examples described with reference to FIGS. 17A-17C, the IV bag may be inverted so that the fill port is oriented downwards for the fill process. The contents of the syringe may then be injected into the IV bag. The robotic arm 318 then conveys the IV bag to the scale station 326 where the IV bag is weighed to confirm the predetermined dose programmed into the RIVA. The robotic arm 318 then moves the IV bag to a bag labeler tray station 342 where a label printed by the printer and labeling station 328 is applied to the IV bag. The robotic arm 318 may move the IV bag to the output scanner station 330, where the information on the ID label is read by the scanner to verify that the label is readable. One or more further verification checks may be performed, examples of which are described elsewhere herein. The IV bag is then taken by the robotic arm 318 and dropped into the IV bag discharge chute 344 where it is available to the pharmacy technician, for example, to be placed in inventory within the hospital pharmacy.

In another embodiment, a vial (or other medical item or container) may be prepared for reconstitution. During the performing of this process by the RIVA 100, the vial may be identified at a vial ID station 346 where, for example, a bar coded label on the vial may be read by a scanner and/or image hardware in combination with image processing software. The captured information may be processed to identify the contents of the vial and correlate it to what is expected. In some implementations, as an alternative to or in combination with bar code scanning, the RIVA 100 may employ pattern matching on the vial using optical scanning techniques. Also, in the reconstitution process, vial mixers 348 may be used to mix the vial contents with the diluent before using it for dosing.

In some embodiments, the robotic manipulator may include apparatus for reading machine readable indicia in the RIVA, including the compounding chamber and/or the storage chamber. For example, the manipulator may include a fiber optic camera for taking images that can be processed to compare to stored image information (e.g., bitmaps). In other examples, the reading apparatus may include optical scanning (e.g., bar code) or RFID (radio frequency identification). Some embodiments may transmit image information wirelessly (e.g., using infrared or RF (radio frequency) transmissions) to a receiver coupled to the RIVA. Such a receiver may be located inside or outside the chamber with the robotic manipulator. Such a reader may be used to read machine readable indicia at various locations in and around the compounding chamber, including through windows and on portions of the storage carousels that are exposed to the compounding chamber.

Figure 4:
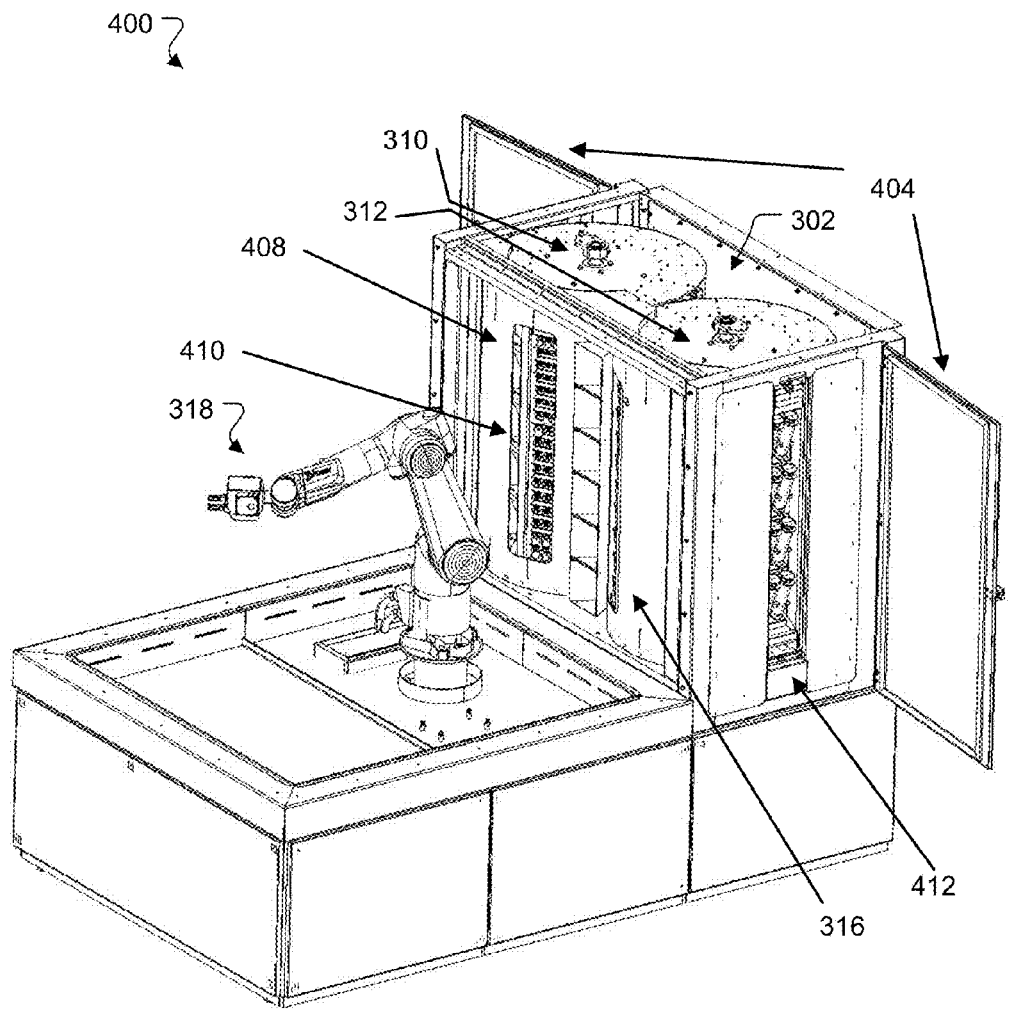
FIG. 4 is a perspective cut-away view showing illustrative details of the apparatus for handling and storing syringes, IV bags, and drug vials in system of FIG. 1.

FIG. 4 shows a perspective cut-away view 400 of at least a portion of an illustrative RIVA, an example of which is the RIVA 100, shows details of the apparatus for handling syringes and IV bags in the RIVA 100. The handling apparatus delivers inventory, including various sizes and types of syringes, vials, or IV bags, to be grasped by the robotic arm 318 in the processing chamber 304. An operator or technician may load/unload inventory racks that store the inventory until delivered to the robotic arm 318. In this example, the carousels 310, 312 may store syringes, vials, and/or IV bags, for example, for use in processes performed in the RIVA 100. The partial view 400 of the RIVA 100 is shown with the much of the processing chamber 304 removed to show the robotic arm 318 and how it can access the inventory chamber 302.

The inventory chamber 302 is shown in this embodiment with loading doors 404, which may be opened to load or remove a rack from either of the carousels 310, 312. The operator puts the RIVA 100 into a loading mode to control a carousel by indexing it away from the robot access position where the curved wall 408 allows a portion of the carousel rack to be presented to a robot access port 410, which is in a portion of the dividing wall 316. The carousels 310, 312 may rotate to align the rack stations on the carousel with the loading doors 404 to allow rack-loading access 412. The carousel can be commanded by the operator to position any one of the rack positions in alignment with the loading access port 412. A rack that is aligned with the access port 412 can be removed and replaced with a rack containing a full load of inventory, or a rack may have its inventory replaced in situ, loading inventory into as little as a single pocket at a time. The racks can be reloaded in any combination of individual racks, including replacing all the racks at one time. At the conclusion of the rack loading, the operator may indicate via the touch screen that the RIVA 100 loading process is complete. This initiates a cycle where the carousel rotates through a 360-degree rotation to allow a barcode reader adjacent to the carousel to read a barcode on each of the racks. This allows the system to update the inventory data and correlate racks and inventory with carousel position information.

In this example, the dividing wall 316, which includes the curved wall 408, that separates the inventory chamber 302 from the processing chamber 304 may allow carousel 310, for example, to perform compounding processes within a substantially aseptic environment within the processing chamber 304, even while the operator is loading carousel 312. In an in situ process, for example as described with reference to FIG. 2, the loading of carousel 312 with the stat order may be carried out while the RIVA 100 is operating out of carousel 310. The dividing wall 316 may be designed to substantially minimize airflow between the inventory chamber 302 to the processing chamber 304. Similarly, an airflow restriction may be set up at the loading door 404 in the inventory chamber 302 to restrict air exchange with ambient air when the rack is in the rack loading position (e.g., aligned with the access port 412) and the door 404 is open, for example.

In one embodiment, the loading door 404 may be coupled to an interlock that requires the loading door 404 to be closed during each advance of the carousel 312 for operator safety. Such an embodiment may also help reduce uncontrolled air exchanges in or out of the inventory chamber 302 while the carousel 312 is rotated.

Figure 5A:
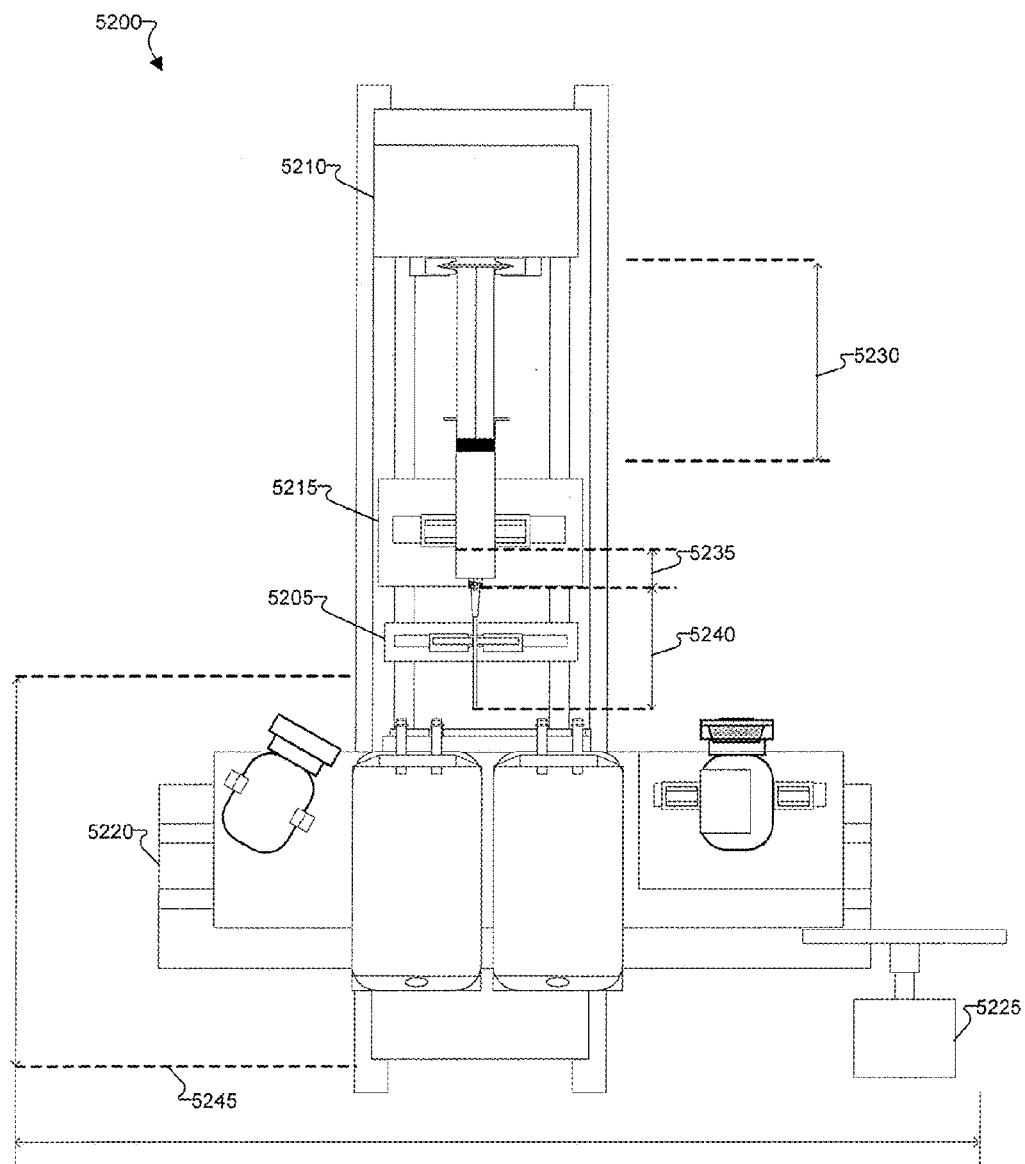
FIGS. 5A-5B show illustrative syringe manipulation at a syringe manipulator needle down station.
Figure 5B:
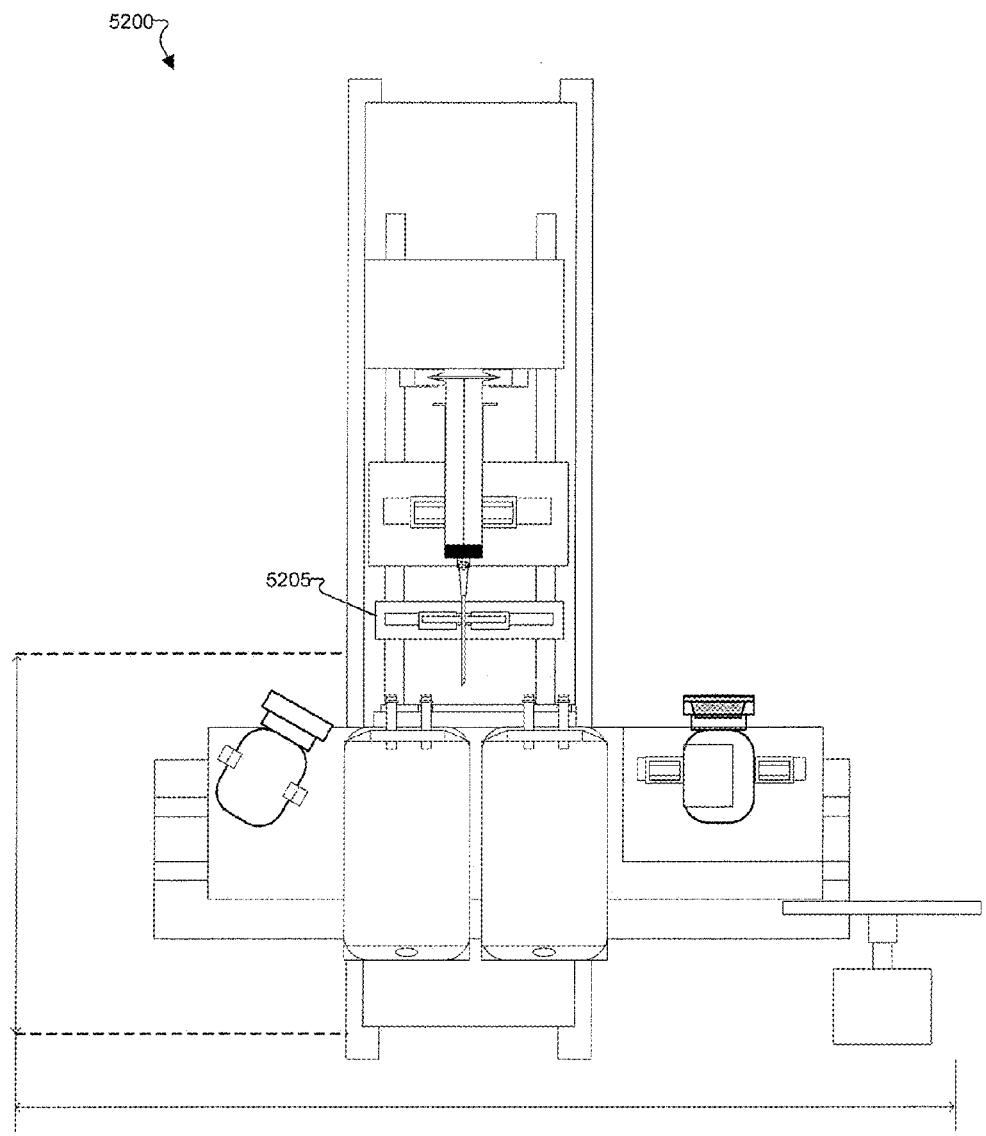

FIGS. 5A-B show an example of syringe decapping at an illustrative syringe manipulator station 5200, such as, in one example, a syringe manipulator station 5200 according to U.S. Pat. No. 7,783,383 B2, shown in and/or described by FIGS. 52-53 thereof. The syringe manipulator station 5200 includes a syringe plunger gripper 5210, a syringe barrel gripper 5210, a vial and bag indexer 5220, and motor and associated motion control hardware 5225. The syringe plunger gripper can slide in a vertical range 5230 to enable the pushing and pulling of the syringe plunger in the syringe barrel. The syringe barrel gripper 5215 can remain stationary. A grip distance 5235 can be the distance from the bottom of the syringe barrel gripper 5215 to the top of a syringe luer lock 4640, as described in U.S. Pat. No. 7,783,383 B2 with reference to FIG. 46. The vial and bag indexer 5220 may move vertically and horizontally in a sliding motion 5245.

Syringes in the APAS or RIVA may be loaded into inventory with needles and needle caps installed, consistent with the illustrative examples shown in FIGS. 5A-5B, or with appropriate closed system transfer device (CSTD) transfer components, consistent with the above discussed implementations. During normal operations, the device can perform operations to remove a needle cap before the syringe can be used in the manipulators, and install an appropriate CSTD transfer component onto the syringe when required. To do this, the syringe may be presented at a manipulator station 5200 that contains a gripper 5205 that holds a needle cap or CSTD transfer component, and a robot performs a pulling away and/or rotational motion that removes the needle cap or attaches the CSTD transfer component. The gripper 5205 can open to release the cap and a sensor can detect the dropping object. This can provide confirmation that the cap has been removed. To ensure that a needle was not removed in the process, or that a syringe did not have a needle installed, the APAS or RIVA can detect the presence or absence of the needle by gripper feedback on the gripper 5205. The fingers on the gripper 5205 can engage the needle within a notch that tightly holds the needle and helps to straighten and/or align the needle for engagement into the port of an IV bag or vial. The gripper 5205 can also provide positional feedback that relates to the distance between the gripper fingers. This positional information can allow for detection of whether or not an object (e.g., a needle) is present between the gripper fingers. The positional information can also be used, depending on finger geometries, to allow for determination of the gauge of the needle present. The positional information can also be used to determine whether a syringe cap is present.

In a similar fashion, the gripper 5205, or a similar provided separate gripper to be used exclusively for IV bags, can manipulate CSTD transfer components onto the ports of the IV bag. That is, the gripper 5205 can receive a CSTD transfer component to be installed onto a port of the IV bag from a robot, and install the CSTD transfer component onto the respective port. As discussed below, the CSTD transfer component includes two port connecting parts that are joined by a flexible member. Here, the gripper 5205 will have predefined instructions as to the dimensions of the IV bag, specifically the port dimensions (spacing, height, etc.), and the dimensions of the CSTD transfer component, specifically (with reference to FIG. 12) the resting distance between a CSTD port 1202 and a spike adapter 1204 via a flexible member 1206. Since the flexible member 1206 may be a wide but thin member, a relative position between the spike adapter 1204 and the flexible member 1206 is known or predictable. Either the spike adapter 1204 or the flexible member 1206 is inserted first, and the manipulator station 5200 will then move the IV bag or the gripper 5205 to insert the other of the spike adapter 1204 and the flexible member 1206 second. To verify a secure connection of the CSTD port 1202 and/or the spike adapter 1204 to the IV bag ports, the CSTD port 1202 and/or the spike adapter 1204, after having been installed onto the IV bag ports, can be pulled up to 5, 10, 20, or 40 lbs, using a sensor of the gripper 5205. If the CSTD port 1202 and/or the spike adapter 1204 disconnect under a given force, an error message or alarm can be generated.

A syringe verification procedure may be used to determine syringe type based on one or more measured diameters. In some cases, a single measurement may uniquely identify a syringe type from among all possible types of syringes that may be loaded. In some other cases, two or more measurements may be required to uniquely identify syringe characteristics.

It is possible within any given hospital that there can be present syringe types from multiple vendors. There may be overlap between syringe sizes, where a given size may exist from more than one vendor. For example, a hospital may use 20 ml syringes from two or even more vendors. It is also possible that as supply contracts are negotiated and renegotiated within a hospital that the common or default syringe manufacturer can change. The APAS or RIVA may be trained to work with one or more syringes from one or more vendors, and similarly, with one or more IV bags.

In various embodiments, the RIVA may use preloaded, predefined syringe and/or IV bag data taken from published manufacturer information which is preinstalled in each delivered RIVA. During processing, the RIVA can determine what syringe sizes are required to fill the queue or orders and those required to reconstitute the vials to fill the drug orders. In this case, operators can receive information about what type and size of syringe may be required to fill a particular order, based on the drug order requirements and the predefined syringe data.

The RIVA can use the syringe to perform fluid transfers. Data about a particular syringe's and/or IV bag's physical characteristics can be used to control the plunger manipulation of the syringe for fluid transfers and the positioning/alignment of the IV bag. To safely and accurately fill drug requests, the syringe and/or IV bag data can be a validated, calibrated and predefined data set that is part of a delivered RIVA. In some embodiments, the RIVA can disallow changing syringe or IV bag data by users. Changing data in the RIVA can therefore be a maintenance operation performed by trained maintenance technicians following proper change control procedures, and not something performed by the device's users.

Figures 5C, 5D, 5E, 5F:
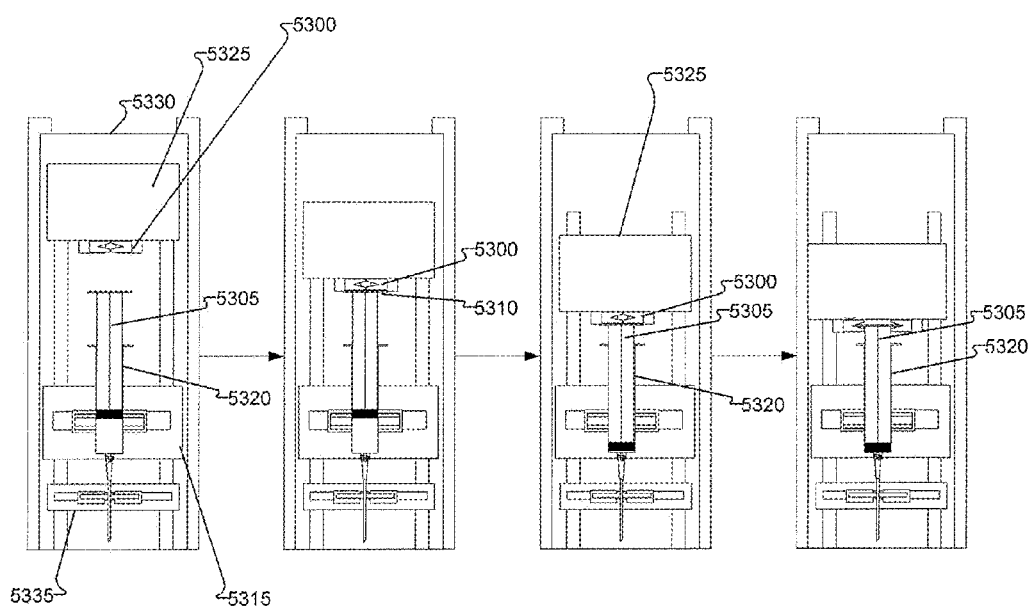
FIGS. 5C-5F show illustrative stages of a syringe plunger maneuver.

FIGS. 5C-F show various stages through which a syringe plunger is maneuvered. FIG. 5C shows a syringe manipulator 5330 which includes an adjustable syringe plunger gripper 5300, an adjustable syringe barrel gripper 5315, a needle gripper 5335 and a moveable carrier 5325. A syringe includes a plunger stem 5305, a plunger stem button 5310 and a barrel 5320.

In various embodiments, a RIVA includes the syringe plunger gripper 5300 with an adjustable width to engage the plunger stem 5305. The syringe plunger gripper 5300 can include fingers to engage the syringe plunger. An actuation system (e.g., one or motors, and associated linkages, gearing) may be operated to control the separation of the fingers on the syringe plunger gripper 5300 to accommodate a variety of sizes of plunger sizes and plunger flange 5310 diameters. The adjustable syringe barrel gripper 5315 can accommodate a variety of different syringe barrel 5320 diameters. The syringe plunger flange 5310 (or stem button) can be engaged for pushing or pulling directly via this adjustable syringe plunger gripper 5300. The gripper 5300 is linked or mounted to the moveable carrier 5325. The carrier 5325 is linked to a vertical slide positioning system, which may be electrically, pneumatically, or hydraulically operated. Movement of the carrier 5325 translates into controllable pushing or pulling of the plunger by operation of the gripper 5300.

Information about the plunger stem 5305 position and the position of the syringe within the syringe barrel grippers 5315 of the syringe manipulator 5330 can be used for accurate fluid transfer operations. The syringe 5320, the needle, and the plunger 5305 can be accurately controlled, for example, to perform operations with the needle down syringe manipulator, in which the syringe can be used to draw diluent from an IV bag, and/or to add fluid to vials for reconstitution.

FIG. 5D shows the syringe plunger gripper 5300 closed engaging the syringe plunger flange 5310. The resistance force of the plunger can be detected as a step increase in force, for example, and the position of the plunger flange may be monitored based on the position of the gripper 5300.

FIG. 5E shows the moveable carrier 5325 moving in a downward direction and pushing the syringe plunger stem 5305 into the syringe barrel 5320, with the plunger fully seated in the barrel. FIG. 5F shows the syringe plunger flange 5310 captured by the gripper 5300 after the gripper 5300 was opened, advanced downward, and closed to engage the syringe flange 5310. From this position, the syringe plunger may be withdrawn controllably from the barrel by upward motion of the carrier 5325.

The RIVA may handle unknown grip height due to, for example, potential variability in how the syringe is seated in inventory. This uncertainty may affect the position of the needle relative to the bag or vial septum (bung), and may result in piercing too deep (not able to draw the expected fluid volume from a vial), or not piercing deep enough (not penetrating the bung or partial penetration that creates an air path and results in, e.g., leaking, aerosolizing, or incorrect fluid transfer). In one embodiment, the syringe manipulator can be used to properly position the syringe for height as follows. The plunger gripper can be closed, and brought down toward the syringe. As the gripper is moved vertically down, the closed fingers can push the plunger stem within the barrel. The system can monitor torque feedback from the slider and when it detects the step change in torque, the plunger has been fully seated within the barrel. The system can then open the plunger stem grippers and engage the plunger stem button. At this point, the system can loosen the grip on the syringe barrel and needle. By sliding the plunger gripper, the system can adjust the height of the syringe to a suitable vertical height.

In another embodiment, the syringe barrel gripper can be opened slightly allowing some slippage of the barrel within the grip. With the plunger gripper in the closed position, the plunger slider can be brought down to the expected height for that size syringe. This maneuver may substantially seat the plunger such that, if the plunger stem is not fully seated, the plunger moves within the barrel of the syringe. With a fully seated plunger, then the barrel moves within the gripper.

Figure 6:
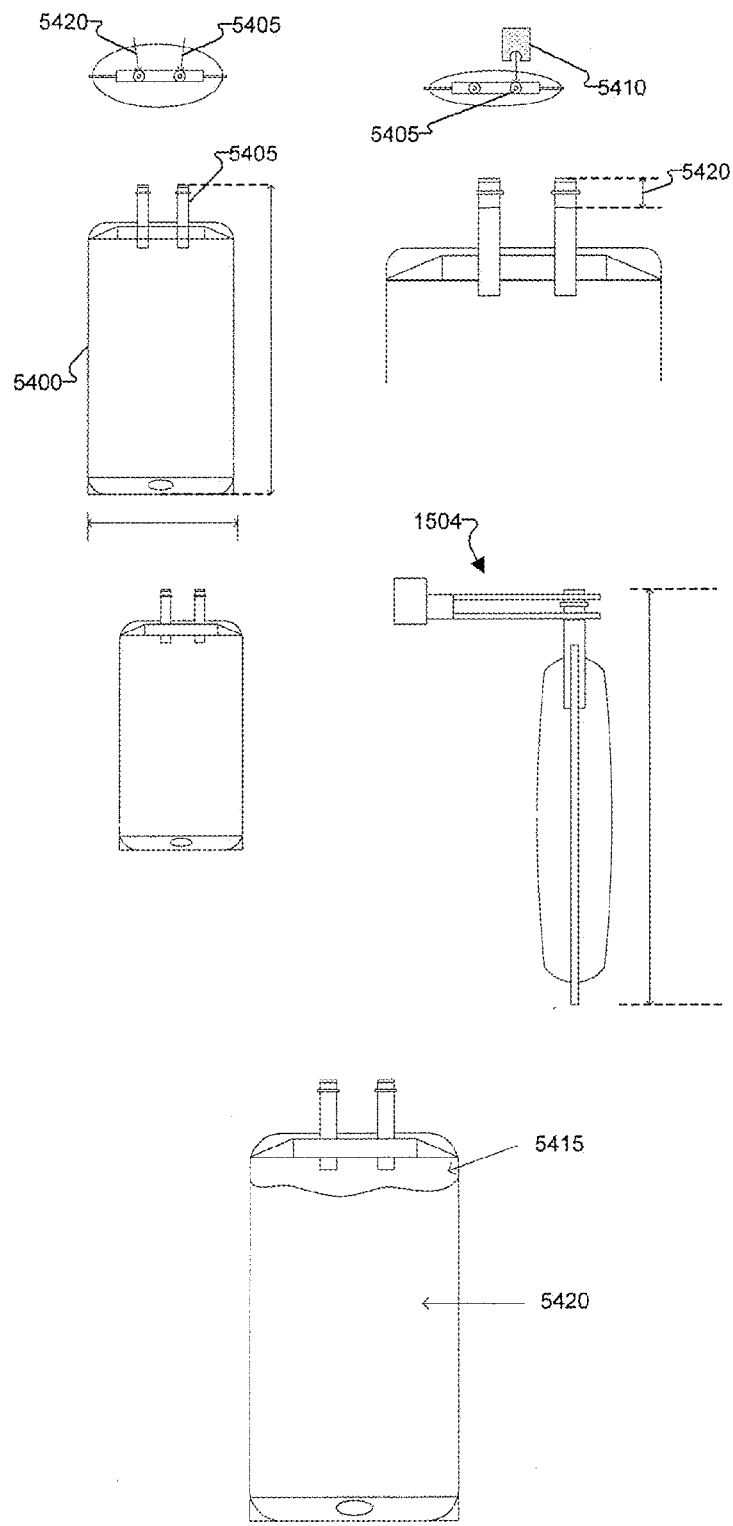
FIG. 6 shows an example of an IV bag on a syringe manipulator.

FIG. 6 shows an IV bag on a syringe manipulator. FIG. 6 shows an IV bag with air space. In an illustrative method, fluid may be drawn from an IV bag with the ports 5405 and 5420 upwards. The robot can take an IV bag 5400 from an inventory rack and place a fill port 5405 into a clip 5410 on a needle down syringe manipulator station, an example of which is described in U.S. Pat. No. 7,783,383 B2 with reference to FIG. 15A. With the IV bag 5400 in this orientation, air space 5415 can be drawn out of the IV bag 5400. A needle can be placed in fill port 5405 by piercing the port an amount equivalent to a bung pierce depth 5420. The method can employ the characteristic that the IV bags can be a sealed container with soft sides such that the bag collapses as air and fluid is drawn from the IV bag. The syringe manipulator can draw the air from the IV bag 5400, and the motion control system can monitor the torque/force feedback on the syringe plunger stem, as described elsewhere herein. There can be a substantial (e.g., a step) change in the force and/or torque when the fluid transfer transitions between transferring air and transferring fluid. In an illustrative example, a blunt fill needle may minimize the air flow back into the bag when the needle is disengaged and subsequently re-engaged into the fill port bung.

In some embodiments, the torque step change on a syringe plunger pull can also be detected by transferring fluid into the IV bag. Moving the syringe plunger stem with the syringe plunger gripper installed and pulling a vacuum within a syringe barrel may involve a detectable change of torque when pulling fluid compared to air. In another embodiment, the syringe plunger stem can be pulled to a known level that is greater than the expected mean air space within the IV bag. The syringe plunger stem can be held in the pulled position and paused while the fluid reaches equilibrium within the syringe barrel. The torque value may drop off as the fluid fills the vacuum that has been formed in the syringe barrel. The next step can be to push the syringe plunger stem so that fluid transfers back into the IV bag, while monitoring the torque value. A step change in torque can be detected when all of the fluid has been transferred back into the IV bag, such that substantially only air is being transferred back into the bag. By monitoring syringe plunger stem position data, it can be determined at what syringe plunger position the step change in torque occurred. The plunger can then be pulled back to that position resulting in an IV bag with the air volume removed.

Identifying syringes that need to be loaded into the RIVA cell may involve identifying several pieces of information. A first piece of information can be a drug order that may include a drug name, a drug quantity/volume, and drug concentration that is independent of any syringe data. A second piece of information can be a site specific drug dispensing table, which defines what size and type of container to use for that drug and size.

For example, at one pharmacy a 2 gram dose of a drug 'X' may be sent to the patients in a syringe. At a different pharmacy, that same drug and dose may be sent in an IV bag. The dispensing table can define site specific preferences for sending orders to patients. The site specific preferences can be independent of any syringe data. A third piece of information can be drug vial reconstitution data, which defines a fluid transfer volume requirement and is part of the determination of the syringe sizes required.

The RIVA can use these items and an algorithm to calculate a fluid volume transfer requirement that is independent of a particular medical container (e.g., syringe). The RIVA can then search the preloaded syringe data to find a predefined syringe of an appropriate size to handle that fluid transfer. When a match is found, the RIVA can then select the syringe's physical dimensions from the preloaded data. If loading is required, the RIVA can output the syringe data to the operator to identify the selected syringe type and size to load.

The RIVA controller can use the pre-loaded syringe data in two illustrative processes: reconstitution and drug order filling.

For reconstitution processes, the RIVA can use published data from drug manufacturers that defines the required diluent type and volume required to reconstitute the powdered drug within a vial. The RIVA use this information to determine a fluid transfer volume for a vial and then automatically can select a reconstitution syringe by using the required volume, and searching the database to find the smallest syringe whose defined volume exceeds the required transfer volume. The RIVA can then calculate syringe plunger travel by using the volume required and information about the interior diameter of the syringe.

For drug order filling processes, fluid can be drawn from vials into the barrel of a syringe and the entire syringe can be dispensed for use by a patient. In this case, the RIVA can use inputted drug order data containing drug name, quantity, concentration and/or optionally patient information. The RIVA can determine, using the drug volume and the dispensing table data, what type of container that drug and volume is to be dispensed in. For example, in one pharmacy, a 2 gram drug order may be dispensed in a bag, while in another it may be dispensed in a syringe, and this can differ from one pharmacy to another. The RIVA cell can then automatically select the smallest size of syringe that exceeds the fluid transfer requirement. The RIVA can then use that syringe's parameters (e.g., interior diameter) to calculate the total plunger displacement, and then to determine the appropriate motion cycling (e.g., plunger push and pull) to maintain appropriate pressure in the draw container (e.g., a vial) which prevents prevent aerosolizing of the content.

In some embodiments, the RIVA may not accept user inputted syringe information, and by design disallows any user input of syringe data for concerns of safety and accuracy of the fluid transfers. For the RIVA, syringe data may be pre-defined and pre-loaded from published manufacturer data.

Some embodiments restrict the type of inventory that can be loaded into the RIVA. For example, a RIVA may allow the operator to select between different, pre-defined syringe types, and verify that the operator loads only the selected type of syringe. In some embodiments, the RIVA may detect what syringe is present in inventory at the time that it is used.

The RIVA may implement methods for ensuring which syringe type has been loaded into the cell. Even if the preferred implementation strategy is to limit the device operations to type A syringes, for example, it may be possible during routine operations that an operator makes a mistake and loads the wrong syringe type. If, for example, the system expects type A syringe but is loaded with a type B syringe having a different interior diameter and/or length. Use of the type B syringe, if undetected, may lead to inaccurate fluid transfer and potentially a drug order error. Apparatus for cross-checking may be implemented to mitigate risks associated with such syringe loading errors by the operator. A certain type syringe may also include a syringe with a pre-installed CSTD component, consistent with that shown in FIG. 13.

The RIVA may use combinations of diameter feedback from various grippers in the system, along with scale information (e.g., syringe and/or IV bag weight when empty), and other techniques in combination to reduce ambiguity as to which syringe is presented to the system. Combinations of independent detection methods may be used to verify a medical container, such as a syringe, vial, or IV bag. For example, combinations of one or more gripper feedbacks and length feedback (e.g., using an optical photo-interrupter detection system), and/or torque feedback (e.g., as a function of position) from the syringe manipulator may be used for container verification. Combinations of these and other methods, such as comparison of stored (trained) image information with captured images from a vision system to identify the container, may be used.

In some embodiments, a separate drug order processing step may take the drug order data and the pre-loaded syringe data and compute the linear travel that the plunger needs to be moved. A command can be placed in a buffer for a controller in the RIVA, for example. In one implementation, this may be a database table.

In one embodiment, a user (e.g., pharmacy staff) cannot override pre-loaded syringe and/or IV bag data in the RIVA by manually inputting data. In this embodiment, the controller may not receive any inputted syringe information, and the controller may not calculate the plunger movement distance using inputted syringe data. The controller that moves the plunger may not receive any inputted syringe data; rather, it may receive preprocessed data that defines the travel distance for the plunger. The motion control hardware translates this into, for example, motor pulse counts for a stepper type motor. The controller may also implement an algorithm to manage (e.g., by maintaining below a stored threshold value) the pressure in a fluid receptacle (e.g., vial or bag) that results in alternating between extending and retracting (e.g., pushing and pulling) the syringe plunger.

The RIVA may use information about the interior diameter of a syringe barrel, for example, to calculate the travel distance for the syringe plunger.

Within an illustrative cell, the RIVA can incorporate a series of linear grippers to hold syringes, vials, CSTD components, IV bag ports, and/or needles. Examples of grippers are described in U.S. Pat. No. 7,783,383 B2 with reference to FIG. 10, and FIGS. 5C-F discussed above. The grippers can be fitted with a variety of fingers that incorporate unique features for improving the hold of the gripper on the cylinders of the syringes and vials, or other parts of the syringes, vials, CSTD components, IV bag ports, and/or needles. Notably, the fingers can incorporate a V-Notch that increases the area of contact on the syringe barrel and the vial body. The gripper fingers can provide feedback via a serial interface to a controller in the RIVA. The feedback can include positional information of the space between the gripper fingers. The RIVA can use this gripper feedback as part of multi-step confirmations of vials and syringes.

IV bags may be used in the RIVA as a source for diluent to reconstitute drugs, as a source for diluting drugs within a syringe, and as a receptacle into which drugs can be injected. Some embodiments may provide mechanisms to verify contents of inputs and outputs related to automated processing of IV bags.

Figure 7A:
FIGS. 7A-7B show illustrative images of IV bags.
Figure 7B:

FIGS. 7A-7B show illustrative images of IV bags that may be used in a RIVA. Pattern matching using a vision subsystem can be used to identify the bags in some embodiments.

Each IV bag may have a varying pattern of folds and warps that may be resolved in order to identify the bag. The RIVA can incorporate a method of de-warping the bag image through image processing. A drained, flat bag can be used to capture a baseline image, and then the RIVA can determine whether or not the sampled bag image can be mapped to the trained image. The RIVA controller, by executing specific software, can attempt to determine a deformation grid that, when applied to the captured image, can result in a good match with the trained image. The RIVA can return a score of how well the de-warped image matches the trained pattern. Alternative methods may include the use of a filled bag as the source for a trained image. In many cases, the areas of interest can curve around the edge of the bag, and use of a flat image may return a lower match score.

In an illustrative embodiment, a RIVA may incorporate multiple independent methods to verify the contents of a medical item, such as an IV bag, vial, and/or syringe. Bar codes may be incorporated in the labeling of IV bags. The RIVA can use bar codes, if they are present on an IV bag, to provide another independent check on the contents of the bag. Vision software may be used to process and decode captured images of the bar code. Optical character recognition software may process images with text to identify contents. Some embodiments may use a separate external bar code reader so that bag ID validation is not dependent on only a single optical system (e.g., vision system and vision software).

In some embodiments, the bar codes can contain a drug identification number, but can also include multiple bar codes or additional information (such as lot number and expiry date) encoded within the bar code. The RIVA controller can include a processor (e.g., digital circuit, ASIC, and/or microprocessor) to parse a bar code and/or to identify the unique sub-elements of the bar code that identify the drug contents. Bar codes may be one or two dimensional.

In some cases the bar code may be on the same face as the bag label information, or it may be on the reverse side of the bag. The RIVA may include a method to capture location and position information on the bar code so that the robot can correctly present the bar code to an bar code reader outside of the compounding chamber. For example, if the bar code is present on the face of the bag, a rotational maneuver with the robot may be executed to present the bar code to an external reader.

In some embodiments, a RIVA may incorporate multiple methods to check a vial's contents. Bar codes may be incorporated in the labeling of the vial. The RIVA can use bar codes, if they are present on the vial, to provide another independent check on the contents of the vial. Vision software may be used to process and decode captured images of the bar code. Some embodiments may use a separate external bar code reader so that the vial identification and/or verification is not dependent on only one vision system for validation.

Bag fluid contents can vary between bags and batches due, for example, to manufacturing tolerances. An illustrative RIVA can incorporate a method of verifying bags by weight and differential weights. A bag that is used for dispensing can be weighed before and after a drug is injected. The differential weight may be used to verify that an appropriate fluid volume was added or removed. A bag that is used for fluid draws can also be weighed before use and this weight can be used to confirm the bag size and the expected fluid contents. For example, a mean empty weight of the bag and the weight of 1 ml of fluid can be preloaded in database tables. Weighing the bag before use, subtracting the weight of the bag material, and dividing the weight by the weight of 1 ml of the fluid can yield an approximate volume of fluid in the bag. This number can be used in the number of draws that can be pulled from the bag. The data tables can contain an expected weight with tolerances for that size bag, but this method can confirm the fluid contents of the bag before use.

Figure 8A:
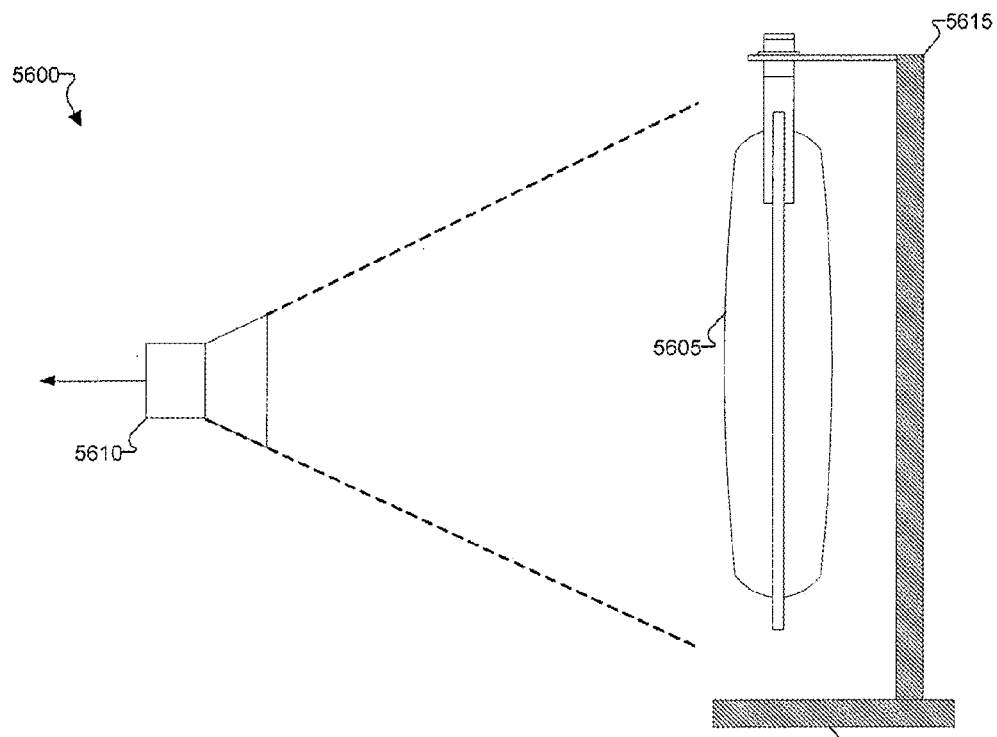
FIGS. 8A-8B show an illustrative system for IV bag identification and confirmation.
Figure 8B:
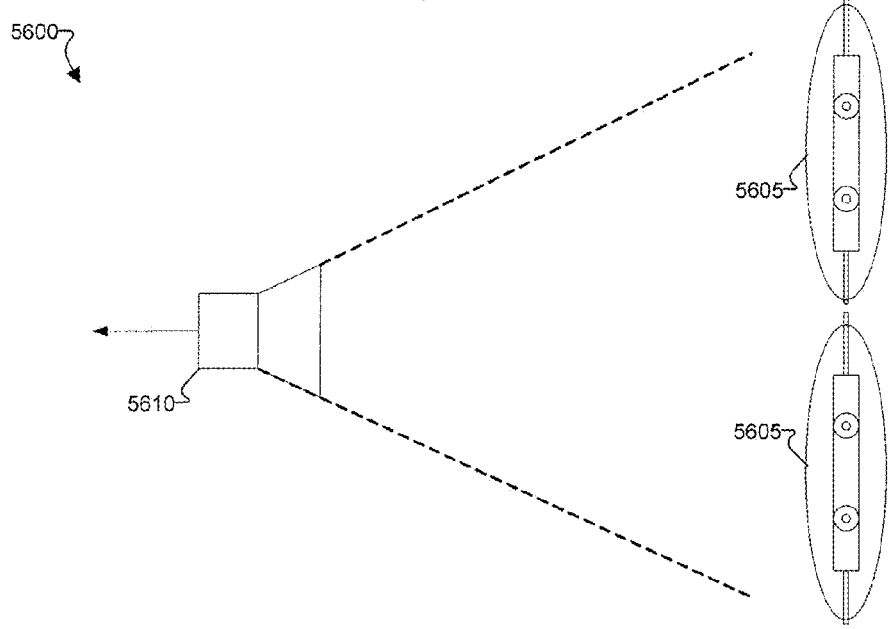

FIGS. 8A-B show an illustrative system for IV bag identification and confirmation in a RIVA. The system 5600 is shown with a side view, FIG. 8A, and a top view, FIG. 8B. The system can be used to identify an IV bag 5605 using vision software for recognition, as described above. A camera 5610 can be used to capture an image of the IV bag 5605 in a holder 5615. The captured image of the IV bag can then be used by the image recognition software for identification. Dose verification can be done by weighing the IV bag on a scale 5620 before, during and/or after the reconstitution process as has been previously described. The weight can be used by the RIVA controller for dose verification purposes. The weight can also be used by the RIVA to determine whether the IV bag 5605 has a CSTD device installed thereon.

In some embodiments, the RIVA can implement a method of using multiple areas of interest to improve the accuracy of the machine vision pattern matching. The areas of interest may include fluid name, and fluid concentrations. In some applications, bags may contain saline, dextrose, or sterile water. In the case of saline and dextrose, the concentrations can be fields that may be discriminated, for example, in standard concentrations of 0.9%, 0.45% and 0.225% concentrations. In various embodiments, the vision system may resolve the drug name and/or the concentration.

In some implementations, visual-based identification may be supplemented or replaced by RFID (radio frequency identification) tags included with the CSTD device or an IV bag. Here, an RFID tag can be used to identify a CSTD IV bag assembly from among other IV bags stored in an inventory rack of the RIVA. Further, the RIVA can use the RFID tag to store the CSTD IV bag assembly into a particular inventory area of the inventory rack, so that later access thereto can be simplified.

In some embodiments, various procedures may be used to verify quality and/or performance of the system. For example, patient and/or package information may be sent for display on a display device when the robot arm retrieves medical items from the storage system. In some examples, more than one code may be read, such as a bar code on a medical item and an associated label that may be printed. The multiple codes may be compared to verify that the codes match. Some hospital systems, for example, may include data entry terminals at which patient data may be entered and transmitted to the RIVA. In some embodiments, a total processing time may be calculated in advance, and may then be compared to an actual processing time. Such information may be used to monitor the performance of the system, and may be used for scheduling and planning purposes by estimating about when certain operations (e.g., batch operations) may be completed and/or additional inventory to be loaded. Such forecast information may be transmitted to the inventory controllers that may prioritize and prepare racks to load onto the storage system to minimize downtime.

Prepared syringes may have syringe caps installed on the luer lock tip substantially to prevent leakage or spilling of the fluid contents, and to protect the contents from contamination. The syringe caps may be stored in sterile packaging trays within a controlled environment. Similarly, IV bags may have caps installed, after a fluid transfer has been completed, to protect the IV bag ports and the contents of the IV bag from contamination. Also, IV bags may have a CSTD device according to this disclosure pre-installed by a pharmacist or another section of the RIVA system prior to using a CSTD IV bag in a fluid operation process.

In an implementation, a gripper assembly is configured to substantially universally grasp and retain syringes, IV bags, and vials of varying shapes and sizes. In an illustrative embodiment, a gripping device may include claws configured to grasp a plurality of different types of IV bags, each type having a different fill port configuration. An example thereof is described with reference to FIGS. 1-9 in US 2009/0067973 A1, filed Sep. 11, 2008. Embodiments may include a controller adapted to actuate a transport assembly to place a fill port of the bag, vial or syringe into register with a filling port such as a cannula located at a filling station, or be equipped with carousel transport systems that are adapted to convey bags, vials, and syringes to the admixture system and deliver constituted medications in bags, vials or syringes to an egress area.

Exemplary procedures implemented by the controller are shown and described by FIGS. 41-44 of U.S. Pat. No. 7,783, 383 B2. An example of the controller is shown in FIG. 9.

FIG. 9 illustrates an exemplary processing system, and illustrates exemplary hardware found in a controller or computing system for implementing and/or executing the processes, algorithms and/or methods described in this disclosure.

As shown in FIG. 9, a processing system in accordance with this disclosure can be implemented using a microprocessor or its equivalent, such as a central processing unit (CPU) and/or at least one application specific processor ASP (not shown). The microprocessor utilizes a computer readable storage medium, such as a memory (e.g., ROM, EPROM, EEPROM, flash memory, static memory, DRAM, SDRAM, and their equivalents), configured to control the microprocessor to perform and/or control the processes and systems of this disclosure. Other storage mediums can be controlled via a controller, such as a disk controller, which can controls a hard disk drive or optical disk drive.

The microprocessor or aspects thereof, in an alternate embodiment, can include or exclusively include a logic device for augmenting or fully implementing this disclosure. Such a logic device includes, but is not limited to, an application-specific integrated circuit (ASIC), a field programmable gate array (FPGA), a generic-array of logic (GAL), and their equivalents. The microprocessor can be a separate device or a single processing mechanism. Further, this disclosure can benefit form parallel processing capabilities of a multi-cored CPU.

In another aspect, results of processing in accordance with this disclosure can be displayed via a display controller to a monitor. The display controller would then preferably include at least one graphic processing unit for improved computational efficiency. Additionally, an I/O (input/output) interface is provided for inputting sensor data from Sensors 1, 2 . . . N, and for outputting control signals to one or more robotic actuators to control various robotic arms and/or grippers.

Further, as to other input devices, the same can be connected to the I/O interface as a peripheral. For example, a keyboard or a pointing device (not shown) for controlling parameters of the various processes and algorithms of this disclosure can be connected to the I/O interface to provide additional functionality and configuration options, or control display characteristics. Moreover, the monitor can be provided with a touch-sensitive interface to a command/instruction interface.

The above-noted components can be coupled to a network, as shown in FIG. 9, such as the Internet or a local intranet, via a network interface for the transmission or reception of data, including controllable parameters. A central BUS is provided to connect the above hardware components together and provides at least one path for digital communication there between.

Figure 10:
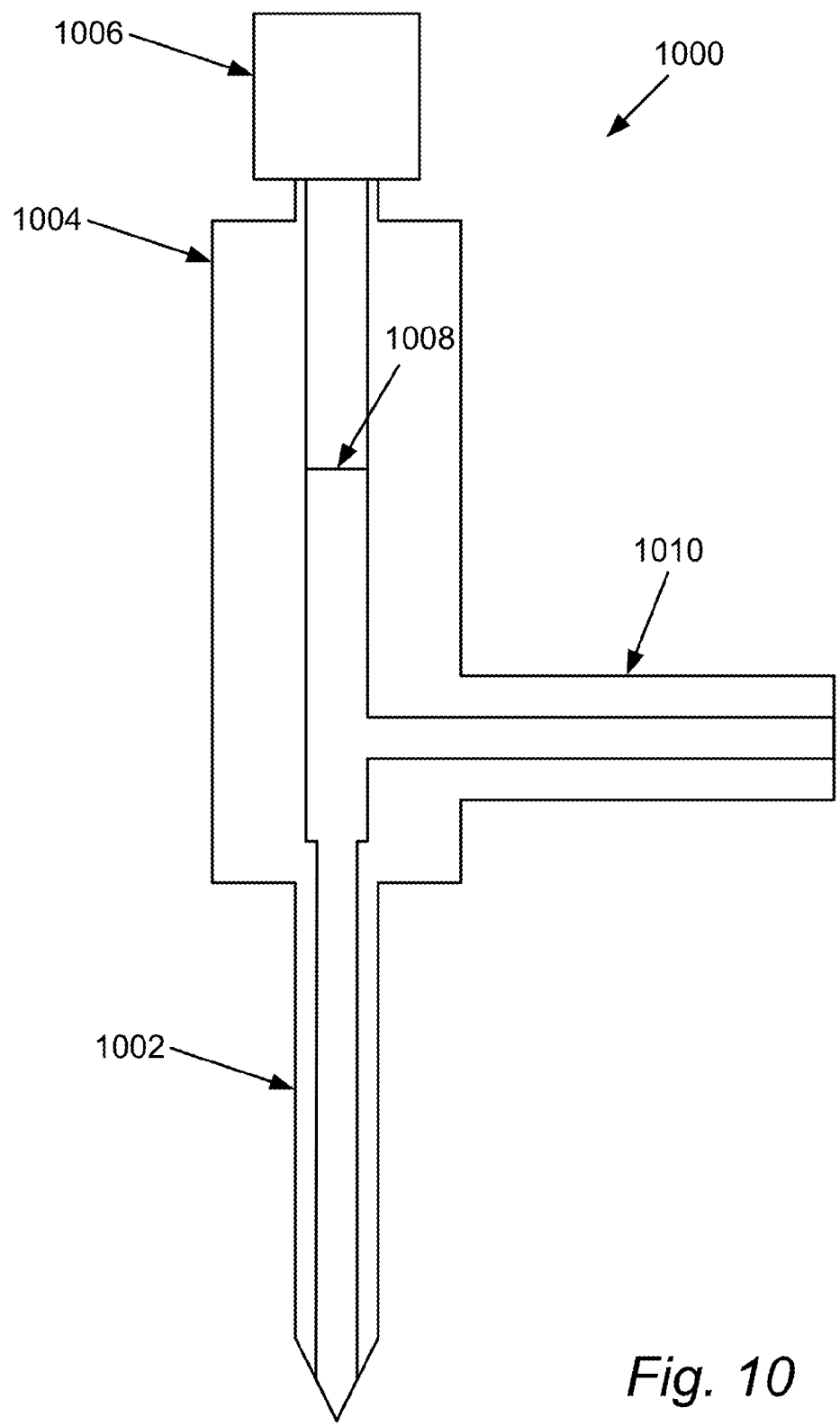
FIG. 10 schematically illustrates a conventional closed system transfer device (CSTD)

A conventional closed system transfer device (CSTD) IV (intravenous) bag adapter 1000 is shown in FIG. 10. The CSTD IV adapter includes a male bag spike 1002 which is inserted into one of at least two ports in, e.g., an IV bag, and a female bag spike receptacle 1004, which is covered to be aseptically clean by a breakaway cover 1006. The female bag spike receptacle 1004 includes a membrane 1008, and is used to withdraw fluid from the bag by insertion of a male spike connected to an administration set (not shown). The leak-free fluid connection port 1010 is shown here in schematic form. The design of various available leak-free connections are proprietary to each device brand. For example, a design from Equashield Medical Ltd. of Israel functions differently than that of a PhaSeal System, which is manufactured by Carmel Pharma AB of Sweden. Typically, a syringe with the mating part of the leak-free connector is attached to the bag adapter connector portion and a drug/fluid is pushed from the syringe into the bag, or a drug/fluid is pulled from the bag into the syringe.

Figure 11:
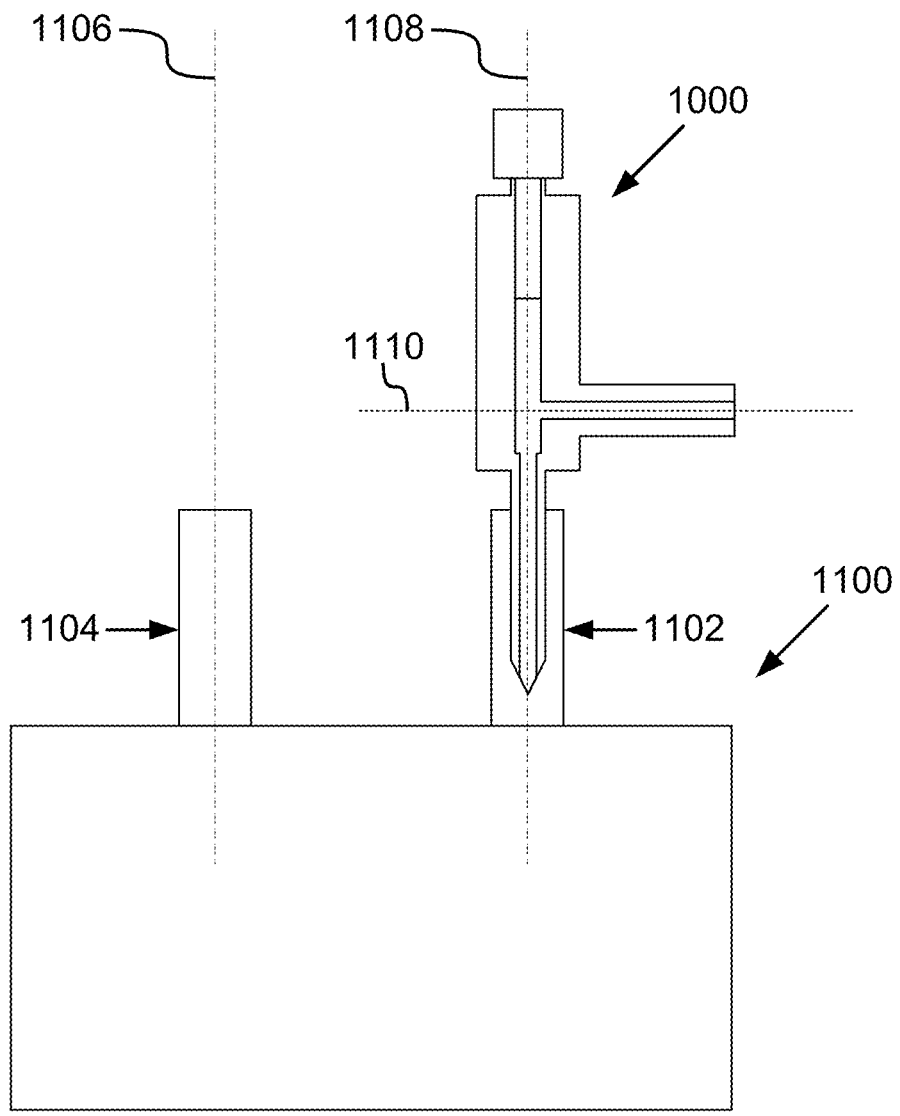
FIG. 11 schematically illustrates a conventional CSTD connected to an IV bag.

FIG. 11 shows the conventional CSTD adapter 1000 inserted into an IV bag 1100 in one of the two ports 1102 and 1104. Typically, one of the ports is designed to accommodate a bag spike 1102, such as that for fitting to the bag adapter 1000, and the other port 1104 to a needle. The composition of the port closures on the bag is different and designed appropriately to seal properly with each cannula type. The insertion axis of the needle port 1104 is along the axis 1106, which is parallel to the insertion axis 1108 for the male bag spike of the bag adapter 1000. The insertion or connection axis 1110 for the leak-free fluid connection port of the bag adapter 1000 is typically 90° (shown) or 45° (not shown) from the needle insertion axis 1106.

The controller for the RIVA may be programmed to distinguish between fluid operations which require a CSTD device and those that do not. In particular, the controller may be programmed to identify a fluid operation which involves a hazardous fluid, and initiate corresponding automated fluid operation algorithms which incorporate the CSTD device.

Figure 12:
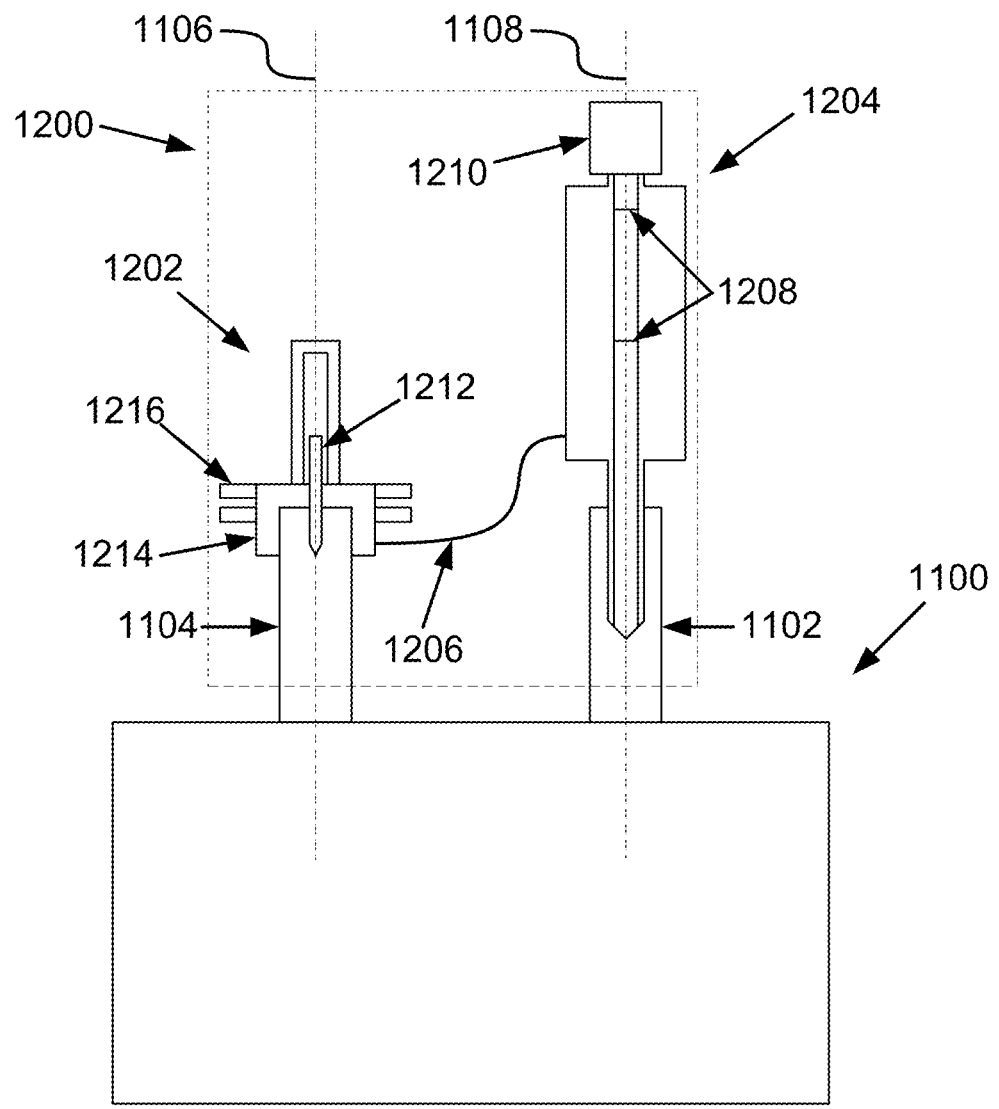
FIG. 12 schematically illustrates a CSTD connected to two ports of an IV bag.

An aspect of this disclosure discussed below relate to a design for a syringe manipulator to allow fluid transfers, with either a syringe/needle or a syringe/CSTD, to be conducted while conserving space and cost. In some regards, this aspect does not require the CSTD ports to be oriented at some 90°, 45° or other angle, as per the conventional arrangement shown in FIG. 11. FIG. 12 illustrates an example of this aspect.

In FIG. 12, a system 1200 is shown, which includes a CSTD leak-free connector 1202 fluidically separated from a spike adapter 1204, where the CSTD leak-free connector 1202 and the spike adapter 1204 are joined by flexible member 1206. The flexible member 1206 allows the system 1200 to be connected to bags with varying port spacing (a distance between the ports 1102 and 1104) and attachment heights (heights of the ports 1102 and 1104—shown at the same height in the drawings).

The flexible member 1206 allows for easy motion to accommodate port height and spacing differences (in the plane of the page as drawn), but is relatively stiff in the normal direction (in/out of the page as drawn) to control the position of the ports such that they do not interfere with automation components. In some respects, the flexible member 1206 resists relative twisting motions between the CSTD leak-free connector 1202 and the spike adapter 1204, so that the CSTD leak-free connector 1202 and the spike adapter 1204 have a natural (unstressed) position of having parallel axes (with respect to a long axis of each of the CSTD leak-free connector 1202 and the spike adapter 1204, that coincide with axes 1106 and 1108). Materials for the flexible member 1206 include metal and plastic, but should be compatible with the environment the adapters are used in. In particular, the material of the flexible member 1206 should be resistant to cleaning and sanitizing agents such as alcohol. A flat and wide member is used in one implementation.

The bag spike adapter 1204 may include two membranes 1208 to minimize a possibility of fluid leakage from the port when the adapter is spiked for subsequent fluid withdrawal during administration. This is an important but optional safety feature for nurses, as the fluids may contain hazardous drugs. The membranes can be made of a suitable plastic material. One embodiment of the upper membrane 1208 (the membrane 1208 that is distal to the port 1102) involves the upper member 1208 including a circular opening designed to be slightly smaller than a spike adapter, such that it will seal upon entry. Another embodiment includes the use of a rupture disc as one of the members 1208, which is perforated by the entry of a spike. The position of the two membranes may be optimized to minimize a possibility of leakage when the administration spike is inserted by ensuring that the upper membrane 1208 fully seals onto the spike prior to the spike puncturing the lower membrane 1208 (the membrane 1208 that is proximate to the port 1102).

In another implementation, not shown, the upper member may be constructively provided for by an engagement with another spike (during usage in the delivering of the contents of the IV bag to a patient), that constructively forms a seal between an exterior surface of a spike and an interior wall of the fluid passage within the bag spike adapter 1204. This may include, not shown a funnel-shaped portion just below the breakaway tab 1210. A friction engagement will then keep the another spike from pulling apart from the bag spike adapter 1204. The breakaway tab 1210 keeps the spike port clean prior to use, where the various components of the system 1200 are sterilized after manufacture to ensure aseptic fluid transfer.

The CSTD port 1202 incorporates a cannula 1212 which is specifically designed to enter the needle port 1104 of an IV bag 1100, and is fluidically connected to allow a leak-free fluid transfer. This cannula may be plastic or metal. The CSTD port body 1214 may incorporate features to allow it to positively lock to the IV bag port 1104. The force required to pull the CSTD port 1202 from the bag 1100 should be at least 5, 10, 20, or 40 lbs. The design of this feature may be unique to the different style of IV bag ports. One embodiment would be to employ reverse facing barbs inside the CSTD port body 1214 that have an interference fit with the bag port. This implementation would be suitable for a bag which has a soft and more or less constant diameter port, such as the Baxter Intravia IV bag, manufactured by Baxter International Inc.

Another embodiment for the locking feature is for bags with at least two significantly different diameter port sections, where an upper diameter (the portion of the port which is distal the IV bag 1100) is larger. Such an IV bag is a Hospira VisIV bag, manufactured by Hospira, Inc. Such a locking feature may include flexible clips that engage a bottom edge of the larger diameter, such as, e.g., in a way similar to a vial cannula attached to a crimp ring.

The CSTD port body 1214 may incorporate geometric gripping and alignment features 1216 to allow robotic grippers to grasp the port as a means of transporting and controlling the entire bag in a repeatable and precise manner. The flexible member 1206 maintains the spike adapter 1204 in a known location with respect to the CSTD port 1202, therefore simplifying the automation design. The alignment features may also be used to hold the system 1200 together with the IV bag 1100 as an assembly in an inventory section of the RIVA, or at other stations. The alignment features 1216 may include two portions such that a first portion is used to locate and hold the assembly in inventory, and a second portion is used by the robot gripper to pick up the assembly and transport it within the machine. A drop-off of the assembly may be the reverse of a pick-up.

Figure 13:
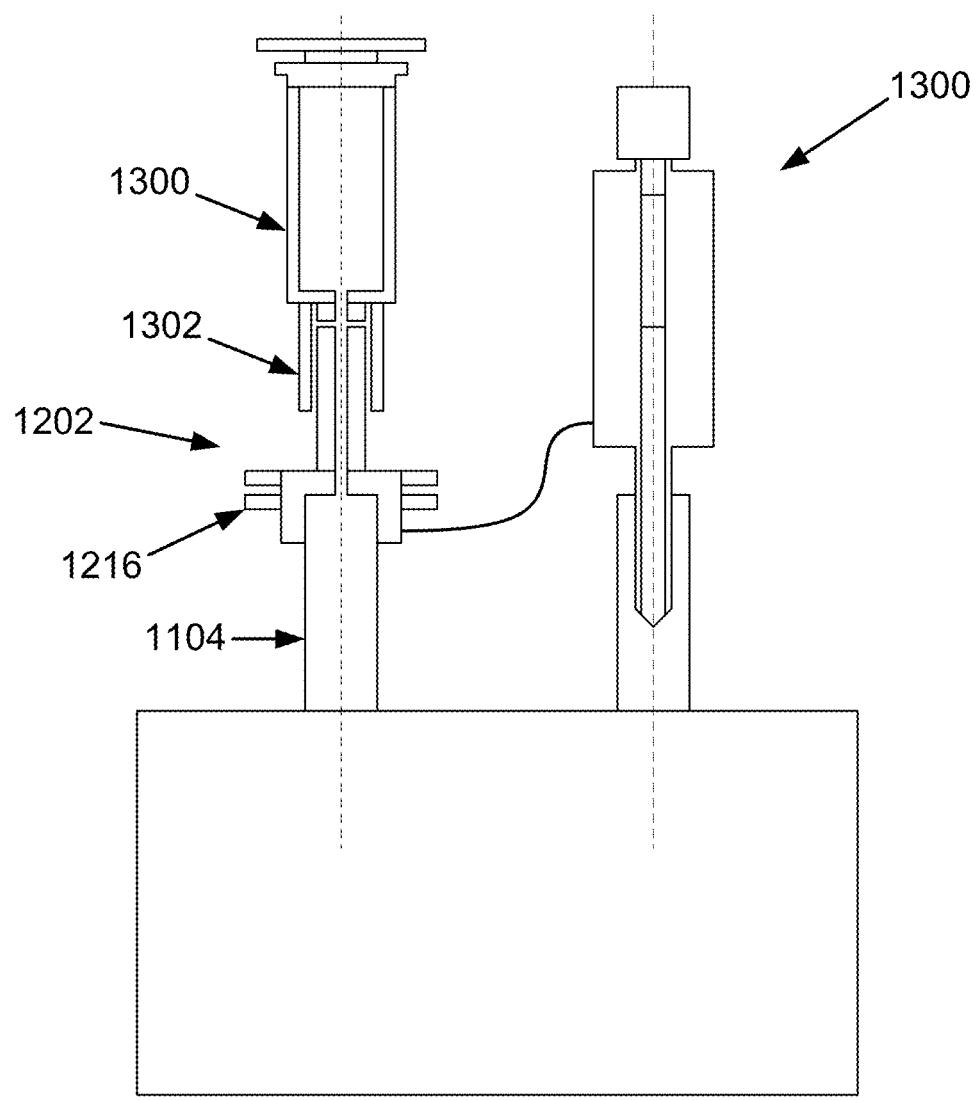
FIG. 13 schematically illustrates a CSTD connected to two ports of an IV bag and a syringe.

FIG. 13 illustrates an example of how the alignment of the CSTD port 1202 is critical to reliable fluid transfer. Automated components, such as the syringe manipulator needle down 5200 station will slide a syringe 1300 fitted with the mating CSTD part 1302 onto the CSTD port 1202 while the CSTD port 1202 is held by the alignment features 1216. The fluid transfer conduit is shown schematically in FIG. 13, and will vary from one CSTD to another. FIG. 13 also shows that the syringe axis is in line with the port axis making it possible to replace the CSTD transfer components 1202 and 1302 with a normal needle and allow it to enter the IV bag needle port 1104 as normal, e.g., as illustrated in FIG. 5A. The use of the axially aligned CSTD transfer ports may therefore reduce automation complexity.

Figure 14:
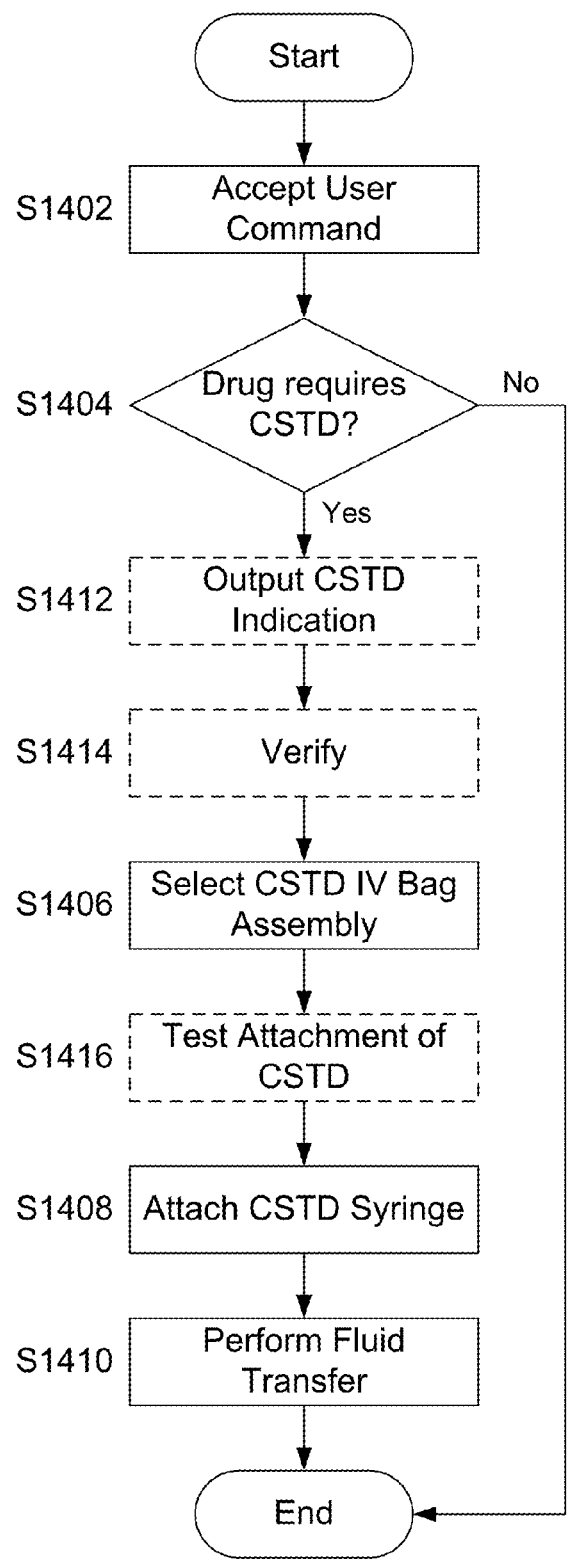
FIG. 14 is an algorithmic flowchart for a CSTD fluid operation.

One exemplary algorithm for the RIVA and the controller to execute for CSTD fluid operations is shown in FIG. 14. In the example illustrated in FIG. 14, the RIVA includes a robotically controlled holder configured to manipulate a IV bag and a CSTD that forms a CSTD IV bag assembly, and a controller including a processor configured to control the holder. Consistent with the above disclosures, the IV bag includes a first fluid port and a second fluid port, the CSTD includes a CSTD port, a spike adapter that is fluidically separated from the CSTD port, and a flexible member connecting the CSTD port to the spike adapter. The spike adapter is connected to the first fluid port of the IV bag, and the CSTD port is connected to the second fluid port of the IV bag.

The controller may be configured to perform a process of accepting a user command to prepare an IV bag with a particular drug (S1402), determining whether the particular drug requires a CSTD (S1402), which can include a determination that the particular drug is a hazardous drug that requires containment, selecting, by the holder, the CSTD IV bag assembly based on the determining (S1406), attaching a CSTD syringe containing the particular drug to the CSTD port (S1408), and performing a fluid transfer of the particular drug between the CSTD syringe and the IV bag via the CSTD port (S1410).

The process can further include outputting an indication to place the CSTD IV bag assembly into an inventory rack of the system (S1412), for example, when such a CSTD IV bag assembly is not pre-installed, and when such a CSTD IV bag assembly is not assembled by the RIVA at, e.g., another station. The process can also include verifying the CSTD IV bag assembly has been placed into the inventory rack of the system (S1414). Verifying at S1414 may include a visual-based verification by image analysis, by the controller, or by RFID tag tracking.

After the CSTD IV bag assembly has been selected at S1406, the RIVA can perform testing (S1416) of the attachment of the CSTD port to the second fluid port of the IV bag by pulling the CSTD port away from the second fluid port of the IV bag and measuring a amount of force applied in the pulling. The testing can be stopped when the amount of force reaches a predefined amount, such as 5, 10, 20, or 40 lbs of force. In the above algorithm, manipulation of the CSTD IV bag assembly can be performed by grasping the alignment features 1216 by the holder (e.g., to move the CSTD IV bag assembly within the RIVA).

In various embodiments, adaptations may include other features and capabilities. For example, some systems may be implemented as a computer system that can be used with implementations described above. For example, various implementations may be implemented in digital electronic circuitry, or in computer hardware, firmware, software, or in combinations of them. An apparatus can be implemented via a computer program product tangibly embodied in an information carrier, e.g., in a machine-readable storage device or in a propagated signal, for execution by a programmable processor; and methods can be performed by a programmable processor executing a program of instructions to perform functions of the invention by operating on input data and generating output. The software can incorporate multi-threading or parallel operations to improve the throughput of the RIVA.

Algorithms and processes can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, implementations on a computer having a display device such as a CRT (cathode ray tube) or LCD (liquid crystal display) monitor for displaying information to the user and a keyboard and a pointing device such as a mouse or a trackball by which the user can provide input to the computer.

The computer system may be implemented as a distributed computing system, and can include clients and servers. A client and server are generally remote from each other and typically interact through a network. The relationship of client and server arises by virtue of computer programs running on the respective computers and having a client-server relationship to each other.

Some embodiments can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of analog or digital data communication, including packet-based messages, on a communication network. Examples of communication networks include, e.g., a LAN, a WAN, wireless and/or optical networks, and the computers and networks forming the Internet.

In various embodiments, systems such as those described herein for handling IV bags and/or syringes, among other items, may communicate information using suitable communication methods, equipment, and techniques. For example, the RIVA controller may communicate with the hospital LAN and/or a hospital pharmacy network using point-to-point communication in which a message is transported directly from the source to the receiver over a dedicated physical link (e.g., fiber optic link, point-to-point wiring, daisy-chain). Other embodiments may transport messages by broadcasting to all or substantially all devices that are coupled together by a communication network, for example, by using omni-directional radio frequency (RF) signals, while still other embodiments may transport messages characterized by high directivity, such as RF signals transmitted using directional (e.g., narrow beam) antennas or infrared signals that may optionally be used with focusing optics. Still other embodiments are possible using appropriate interfaces and protocols such as, by way of example and not intended to be limiting, RS-232, RS-422, RS-485, 802.11a/b/g, Wi-Fi, Ethernet, IrDA, FDDI (fiber distributed data interface), token-ring networks, or multiplexing techniques based on frequency, time, or code division. Some implementations may optionally incorporate features such as error checking and correction (ECC) for data integrity, or security measures, such as encryption (e.g., WEP) and password protection.

A number of implementations have been described. Nevertheless, it will be understood that various modifications may be made without departing from the spirit and scope of this disclosure. For example, advantageous results may be achieved if the steps of the disclosed techniques were performed in a different sequence, if components in the disclosed systems were combined in a different manner, or if the components were replaced or supplemented by other components. The functions, processes and algorithms described herein may be performed in hardware or software executed by hardware, including computer processors and/or programmable circuits configured to execute program code and/or computer instructions to execute the functions, processes and algorithms described herein. Additionally, some implementations may be performed on modules or hardware not identical to those described. Accordingly, other implementations are within the scope that may be claimed.

The invention claimed is:

1. A robotic intravenous automation system, comprising:
   a robotically controlled holder configured to manipulate an intravenous (IV) bag and a closed system transfer device (CSTD) that form a CSTD IV bag assembly; and
   a controller including a processor configured to control the holder,
   wherein
   the IV bag includes a first fluid port and a second fluid port,
   the CSTD includes a CSTD port, a spike adapter that is fluidically separated from the CSTD port, and a flexible member connecting the CSTD port to the spike adapter,
   the spike adapter is connected to the first fluid port of the IV bag, and
   the CSTD port is connected to the second fluid port of the IV bag;
   wherein the controller is configured to control the holder to perform a process of:
   attaching the spike adapter to the first fluid port of the IV bag;
   grasping the CSTD port based on a predefined dimensional characteristic of the CSTD port stored in the controller;
   manipulating the CSTD port, flexing the flexible member; and
   attaching the CSTD port to the second fluid port of the IV bag.

2. The system according to claim 1, wherein the process of further comprises:
   accepting a user command to prepare an IV bag with a particular drug;
   determining whether the particular drug requires a CSTD;
   selecting, by the holder, the CSTD IV bag assembly based on the determining;
   attaching a CSTD syringe containing the particular drug to the CSTD port; and
   performing a fluid transfer of the particular drug between the CSTD syringe and the IV bag via the CSTD port.

3. The system according to claim 2, wherein the process further comprises:
   outputting an indication to place the CSTD IV bag assembly into an inventory rack of the system; and
   verifying the CSTD IV bag assembly has been placed into the inventory rack of the system.

4. The system according to claim 3, wherein the verifying includes a visual-based verification by image analysis.

5. The system according to claim 2, wherein the process further comprises:
   testing the attachment of the CSTD port to the second fluid port of the IV bag by pulling the CSTD port away from the second fluid port of the IV bag and measuring a amount of force applied in the pulling; and
   stopping the testing when the amount of force reaches a predefined amount.

6. The system according to claim 5, wherein the predefined amount is 5, 10, 20, or 40 lbs.

7. The system according to claim 1, wherein the CSTD port includes an alignment structure that coincides with a particular alignment between the CSTD port and the IV bag, in which the holder and controller can distinguish an alignment of the CSTD IV bag assembly by the alignment structure, and in which the holder can manipulate the CSTD IV bag assembly by the alignment structure.

8. The system according to claim 1, wherein the system further comprises an inventory rack, and wherein the CSTD IV bag assembly is pre-installed into the inventory rack.

9. A closed system transfer device (CSTD) assembly, comprising:
a CSTD port;
a spike adapter that is fluidically separated from the CSTD port;
a flexible member connecting the CSTD port to the spike adapter; and
an IV bag including a first fluid port and a second fluid port;
wherein the spike adapter is connected to the first fluid port of the IV bag;
wherein the CSTD port is connected to the second fluid port of the IV bag; and
wherein the CSTD port includes reverse facing barbs on an interior portion thereof that contacts an exterior of the second fluid port of the IV bag to positively lock the CSTD port to the second fluid port of the IV bag.

10. The CSTD assembly according to claim 9, wherein removing the CSTD port from the second fluid port requires at least 40 lbs of force.

11. The CSTD assembly according to claim 9, wherein the CSTD port includes an alignment structure configured to be grasped by a robotic arm for manipulating the CSTD assembly.

12. The CSTD assembly according to claim 9, wherein the CSTD port includes a cannula, and the spike adapter includes one or two membranes.

13. The CSTD assembly according to claim 9, wherein the flexible member has a relatively long, thin and wide cross section to inhibit selected movement between the CSTD port and the spike adapter.

14. The CSTD assembly according to claim 13, wherein the flexible member resists a relative twisting motion between the CSTD port and the spike adapter, so that the CSTD port and the spike adapter have a natural un-stressed position of having parallel axes, with respect to a long axis of each of the CSTD port and the spike adapter.

15. A closed system transfer device (CSTD) assembly, comprising:
a CSTD port, wherein the CSTD port includes a cannula;
a spike adapter that is fluidically separated from the CSTD port, wherein the spike adapter includes one or two membranes; and
a flexible member connecting the CSTD port to the spike adapter.

16. The CSTD assembly according to claim 15, further comprising an IV bag including a first fluid port and a second fluid port;
wherein the spike adapter is connected to the first fluid port of the IV bag; and
wherein the CSTD port is connected to the second fluid port of the IV bag.

17. The CSTD assembly according to claim 15, wherein the CSTD port includes an alignment structure configured to be grasped by a robotic arm for manipulating the CSTD assembly.

18. The CSTD assembly according to claim 15, wherein the flexible member has a relatively long, thin and wide cross section to inhibit selected movement between the CSTD port and the spike adapter.

19. The CSTD assembly according to claim 15, wherein the flexible member resists a relative twisting motion between the CSTD port and the spike adapter, so that the CSTD port and the spike adapter have a natural un-stressed position of having parallel axes, with respect to a long axis of each of the CSTD port and the spike adapter.

20. An IV bag assembly, comprising:
an IV bag including a first fluid port and a second fluid port, wherein the IV bag has a horizontal plane, a vertical plane, and a normal plane; wherein the normal plane is perpendicular with respect to the horizontal and vertical planes; and
a closed system transfer device (CSTD) comprising
a spike adapter connected to the first fluid port of the IV bag,
a CSTD port that is fluidically separated from the spike adapter and that is connected to the second fluid port of the IV bag; and
a flexible member connecting the spike adapter and the CSTD port;
wherein the flexible member can move between the first fluid port and the second fluid port in the longitudinal plane and the vertical plane and is relatively stiff in the normal plane.

21. The CSTD assembly according to claim 20, wherein the flexible member has a relatively long, thin and wide cross section to inhibit selected movement between the CSTD port and the spike adapter.

22. The CSTD assembly according to claim 20, wherein the flexible member resists a relative twisting motion between the CSTD port and the spike adapter, so that the CSTD port and the spike adapter have a natural un-stressed position of having parallel axes, with respect to a long axis of each of the CSTD port and the spike adapter.

23. The CSTD assembly according to claim 20, wherein the CSTD port comprises a cannula.

24. The CSTD assembly according to claim 20, wherein the CSTD port comprises an alignment structure configured to be grasped by a robotic arm for manipulating the CSTD assembly.

* * * * *